US011660367B2

(12) United States Patent
Nanayakkara et al.

(10) Patent No.: US 11,660,367 B2
(45) Date of Patent: May 30, 2023

(54) AIRBORN PATHOGEN DISENFECTING SYSTEM FOR AN HVAC SYSTEM

(71) Applicants: Lakdas Nanayakkara, Boca Raton, FL (US); Pravin Nanayakkara, Boca Raton, FL (US)

(72) Inventors: Lakdas Nanayakkara, Boca Raton, FL (US); Pravin Nanayakkara, Boca Raton, FL (US)

(*) Notice: Subject to any disclaimer, the term of this patent is extended or adjusted under 35 U.S.C. 154(b) by 91 days.

(21) Appl. No.: 17/244,670

(22) Filed: Apr. 29, 2021

(65) Prior Publication Data

US 2022/0347336 A1    Nov. 3, 2022

(51) Int. Cl.
*A61L 9/20* (2006.01)
*A61L 9/14* (2006.01)

(52) U.S. Cl.
CPC ............... *A61L 9/20* (2013.01); *A61L 9/14* (2013.01); *A61L 2209/12* (2013.01); *A61L 2209/14* (2013.01); *A61L 2209/16* (2013.01)

(58) Field of Classification Search
None
See application file for complete search history.

(56) References Cited

U.S. PATENT DOCUMENTS

2010/0132715 A1* 6/2010 Litz ..................... A62B 7/10
128/207.12
2014/0097266 A1* 4/2014 Habbel ............... B65D 83/262
239/69
2020/0245790 A1* 8/2020 Lewis .................. A61F 7/0085
2022/0031139 A1* 2/2022 Chen .................... A47L 11/293

FOREIGN PATENT DOCUMENTS

CN     111397016 A  *  7/2020  ............. F24F 11/74
KR   20090044661 A  *  5/2009

OTHER PUBLICATIONS

Khao, Q. CN111397016A—translated document (Year: 2020).*
Zhao, Q. CN111397016A—translated document (Year: 2020).*
Jung, S. KR20090044661A—translated document (Year: 2009).*

* cited by examiner

*Primary Examiner* — Jelitza M Perez
(74) *Attorney, Agent, or Firm* — Melvin K. Silverman

(57) ABSTRACT

The present invention provides for a system for disinfecting air circulated in an HVAC system. The system includes a multi-phase system, wherein the multi-phase system comprises at least six segments, with at least one segment representing each of at lease one air intake, at least one air handler, and at least one connecting ductwork. The system has at least one interchangeable filter, wherein each filter in said at least one interchangeable filter is an elongate three-dimensional grid with a series of openings to allow circulated are to flow over the air filter's elongate surfaces. The system also has a plurality of ultraviolet lights, and an airborne disinfecting system with at least one spray nozzle mounted to said at least one connecting duct, wherein a supply hose connects said at least one spray nozzle to at least one reservoir of disinfectant.

9 Claims, 40 Drawing Sheets

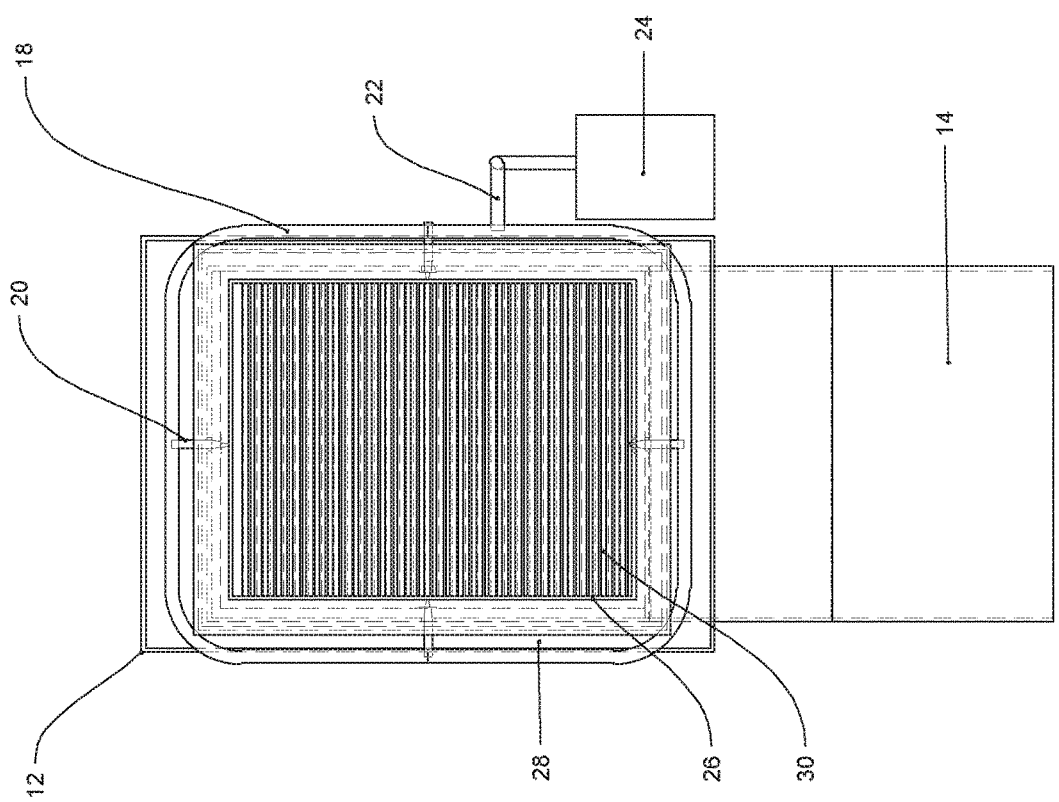

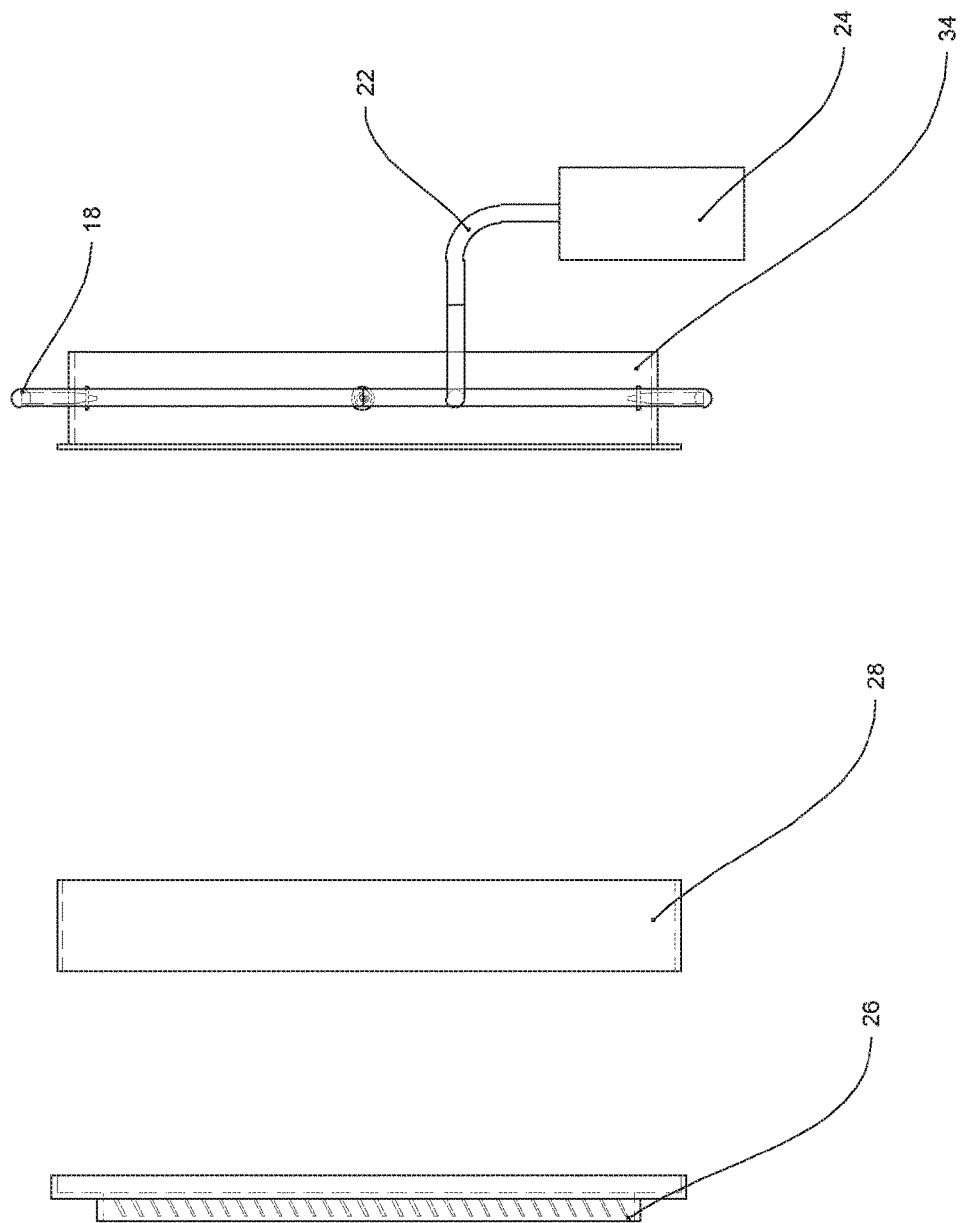

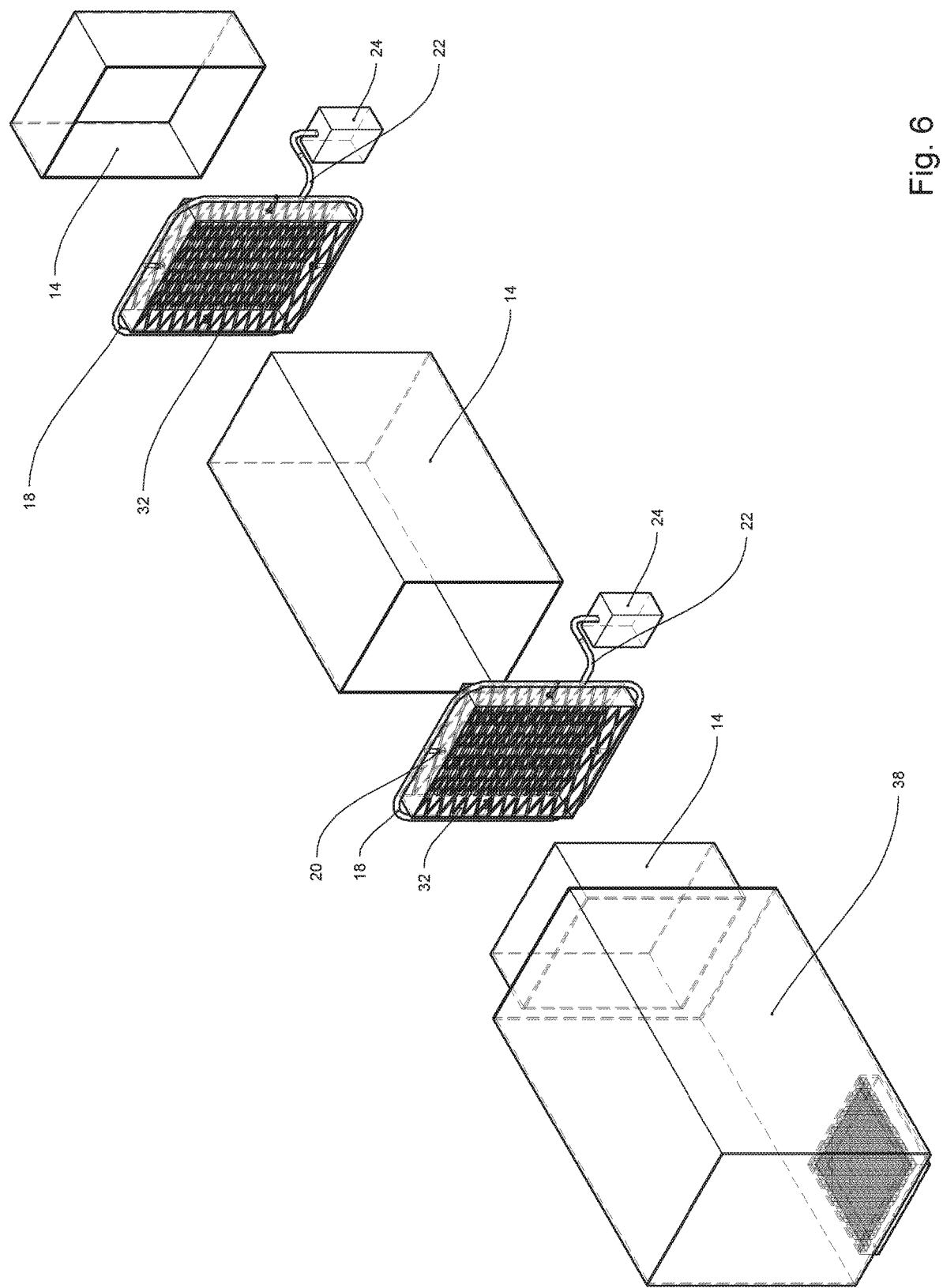

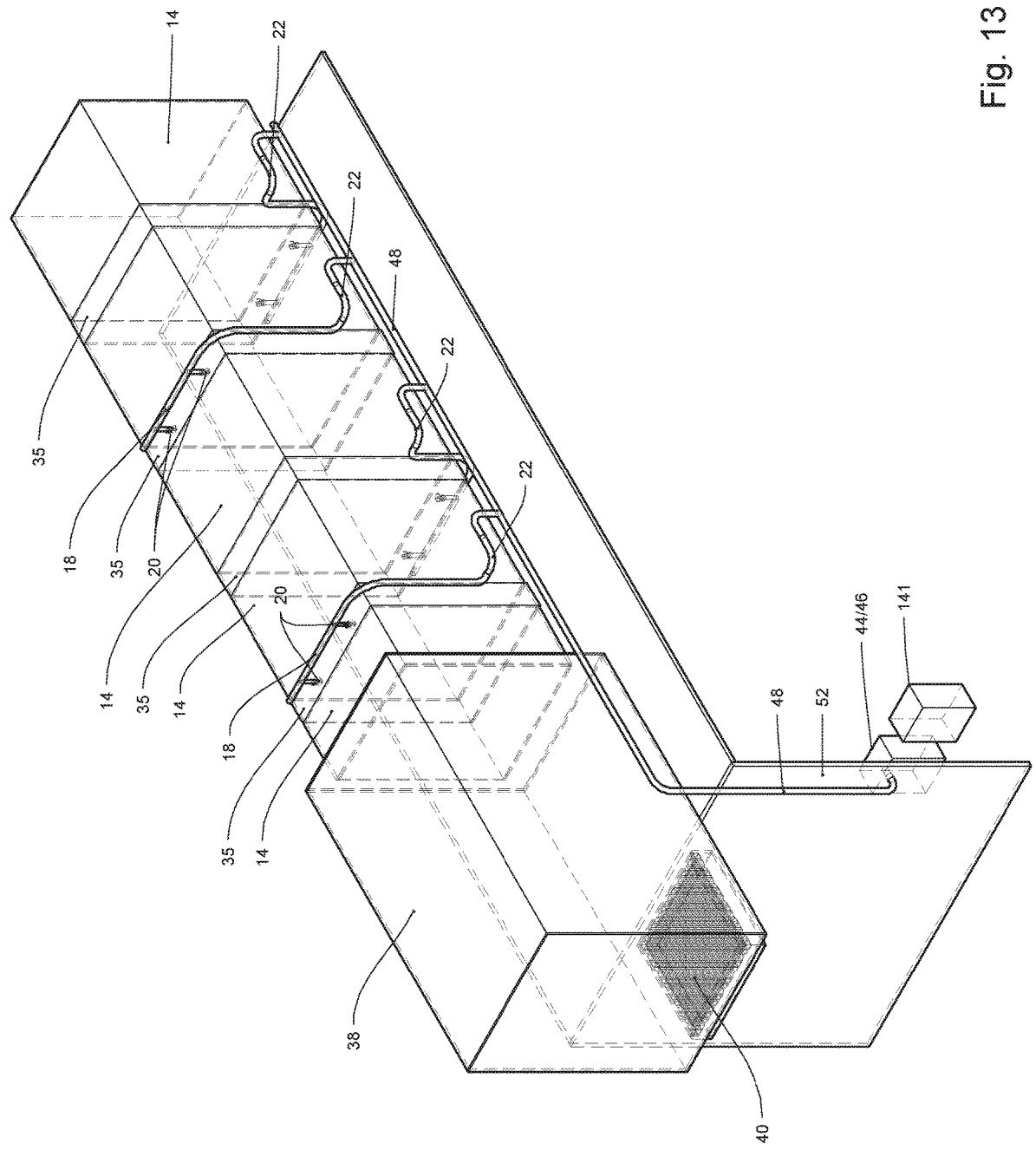

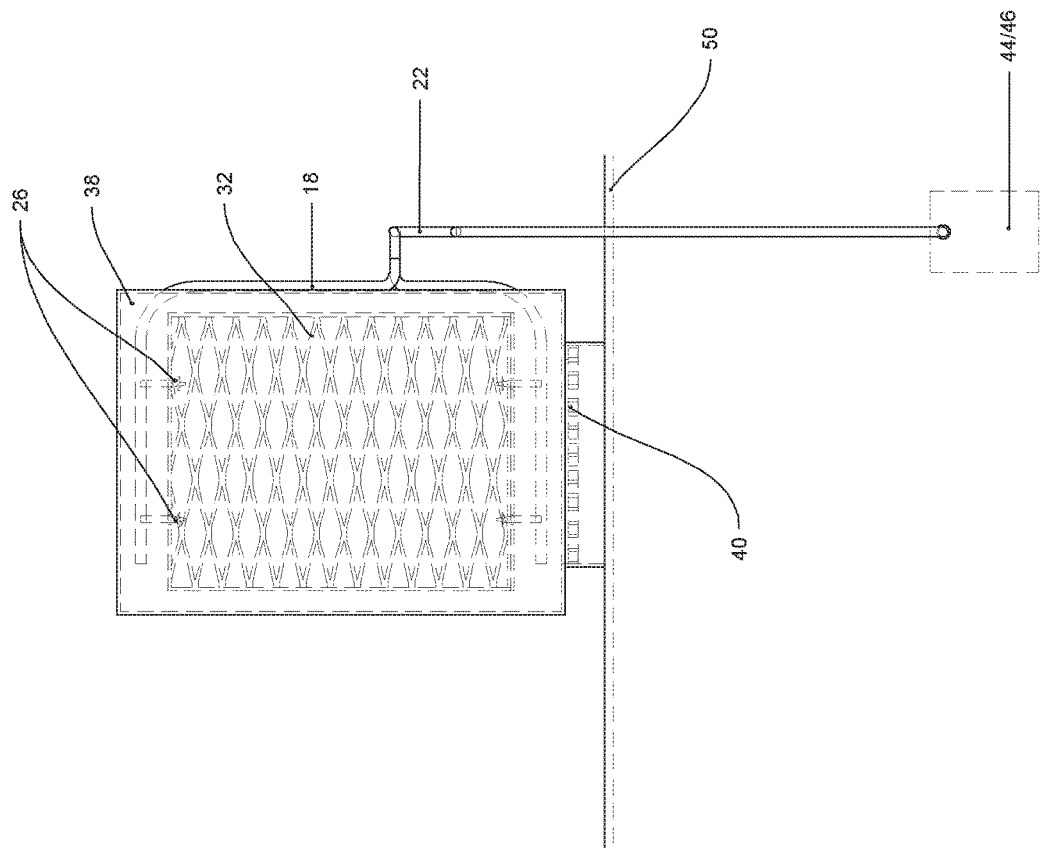

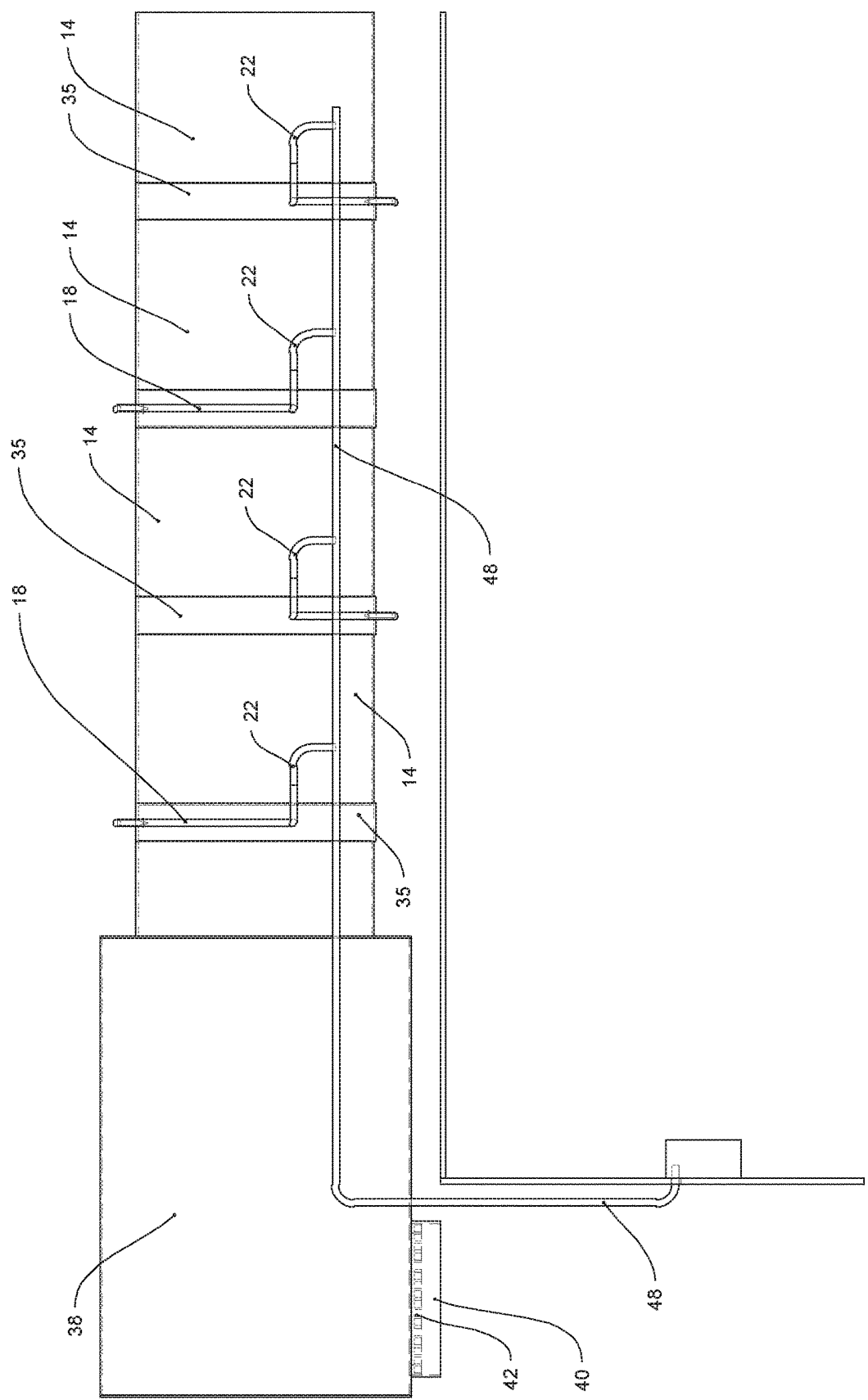

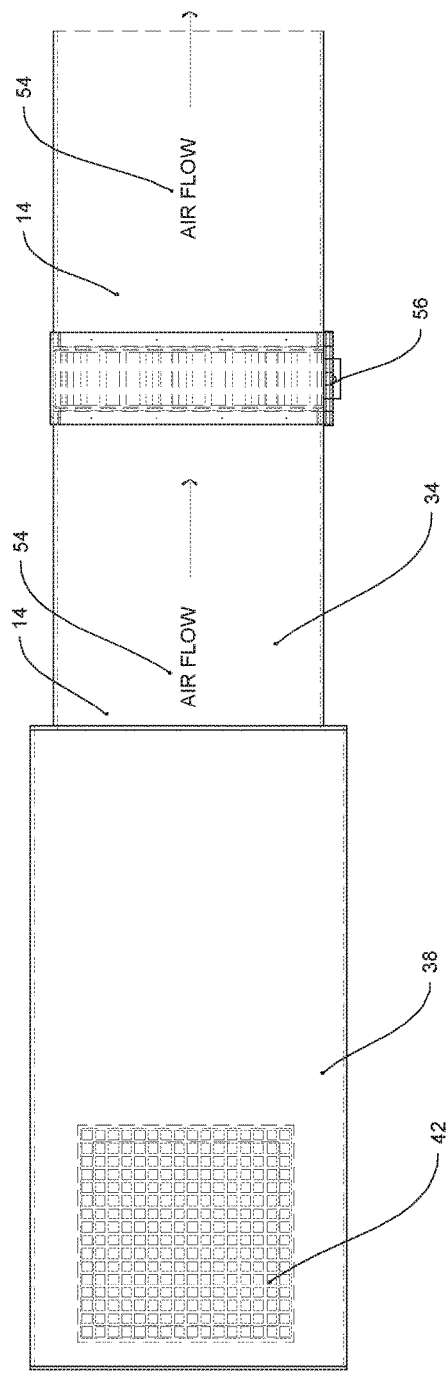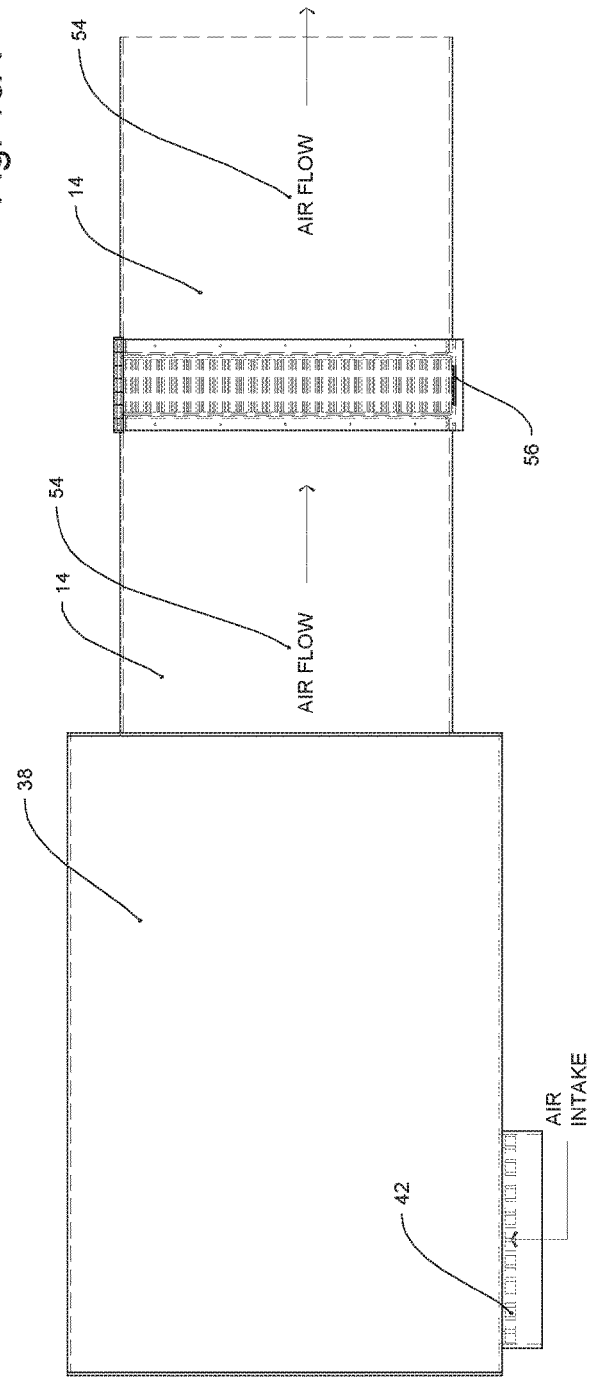

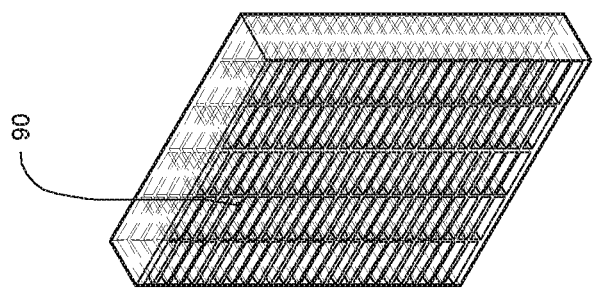
Fig. 19C
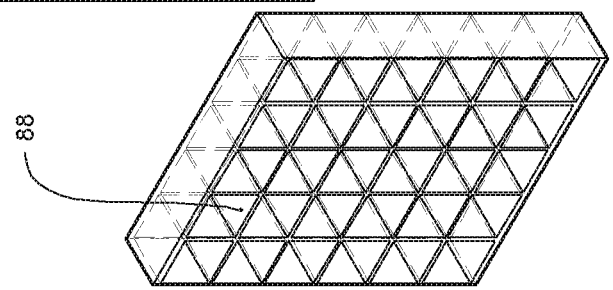
Fig. 19B
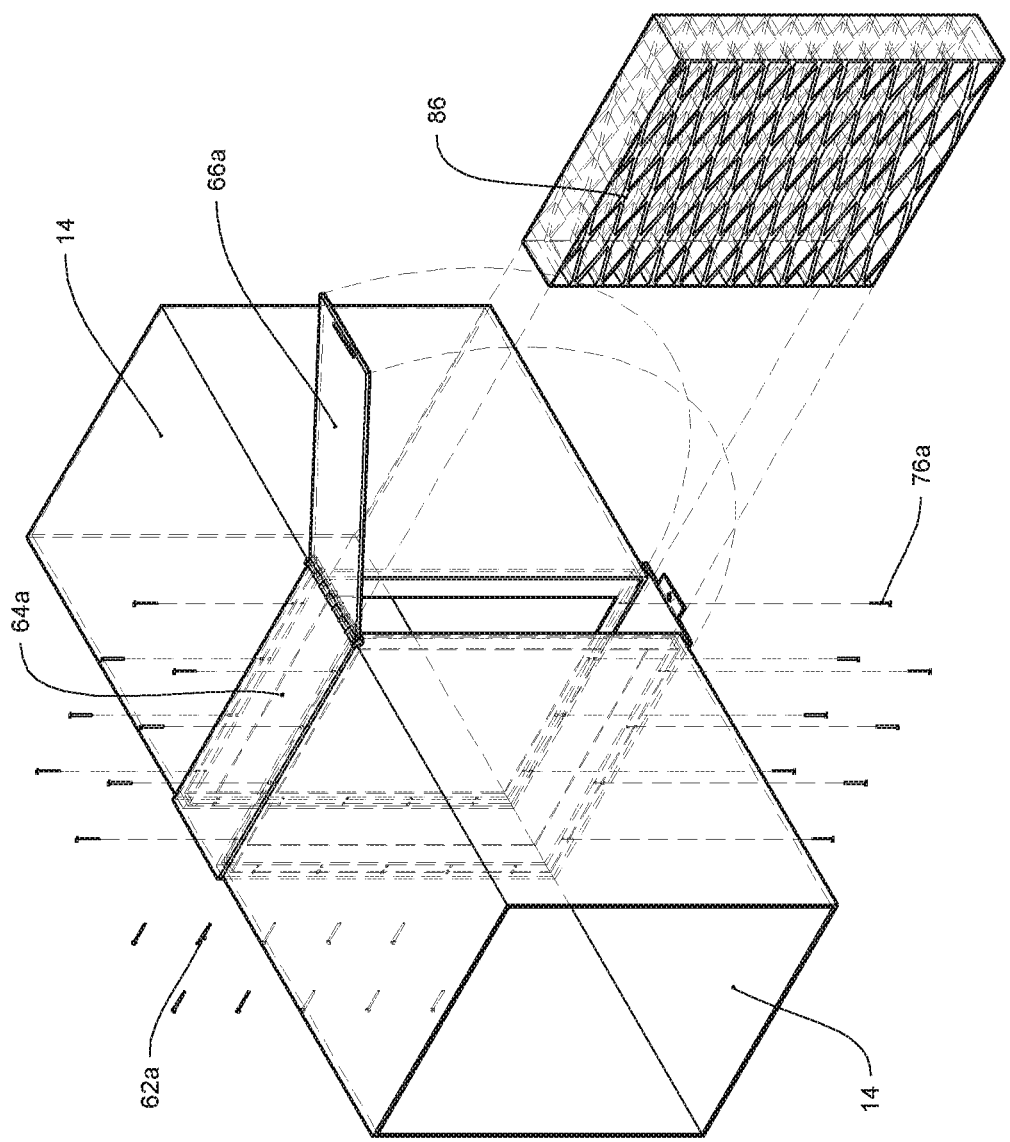
Fig. 19A
Fig. 18D

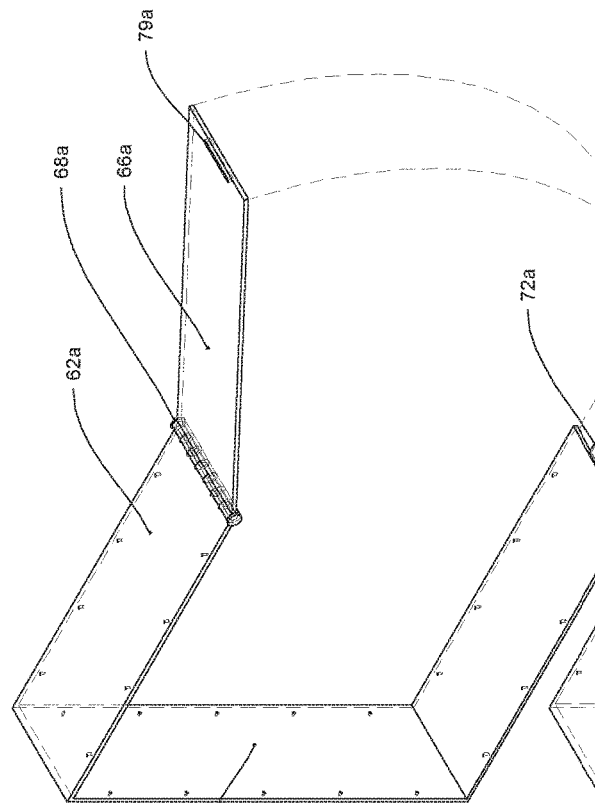
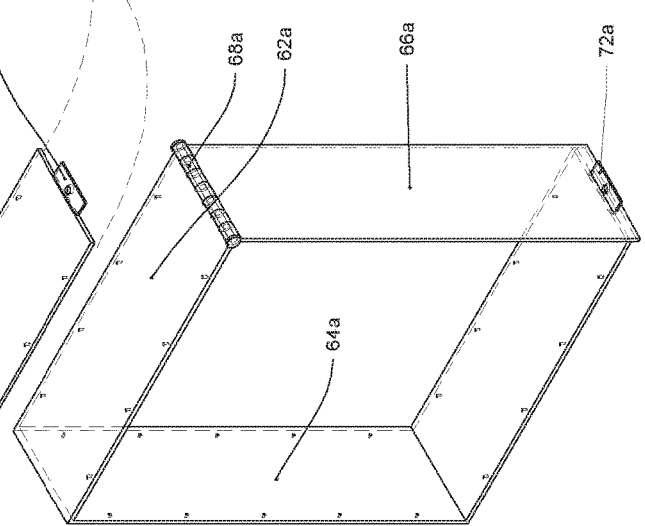
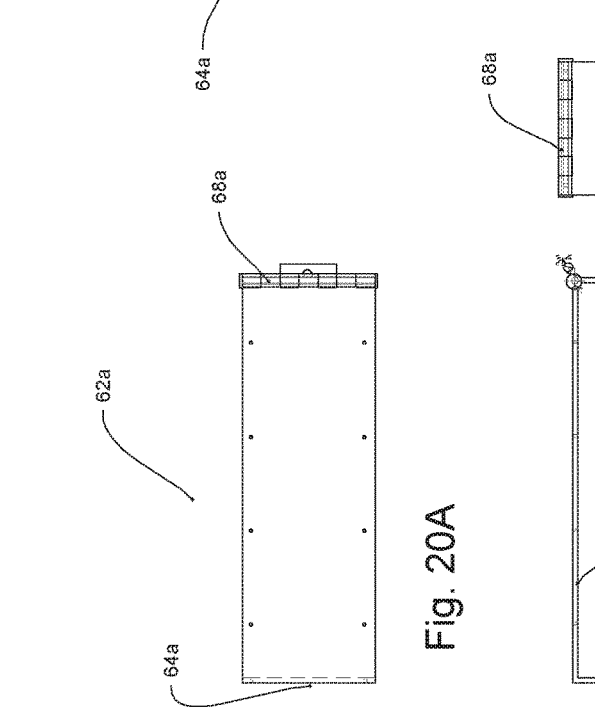
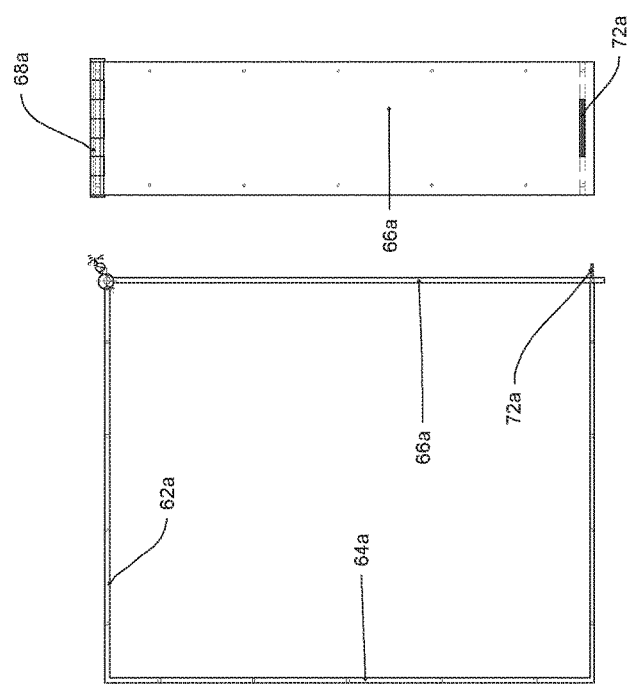

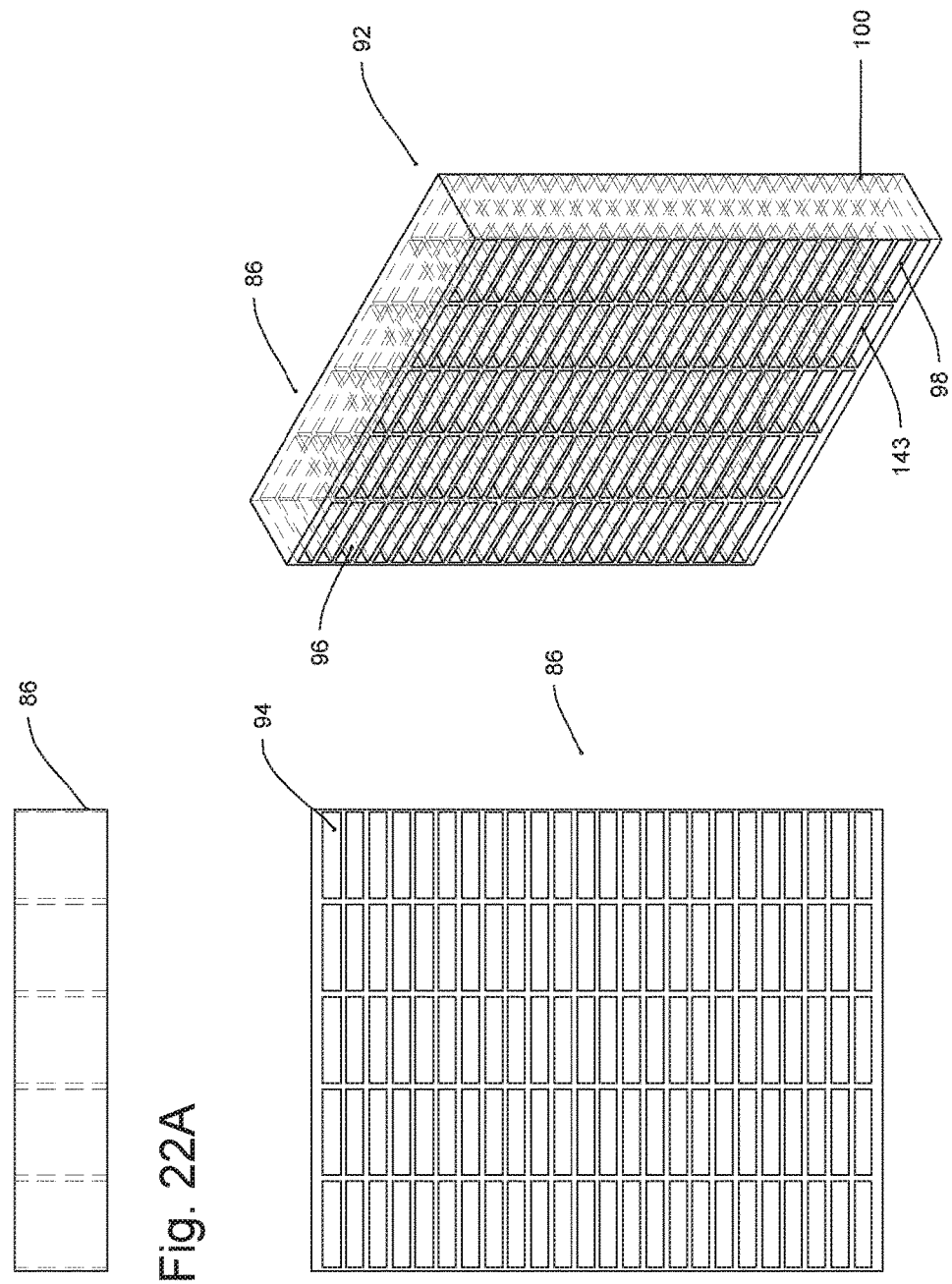

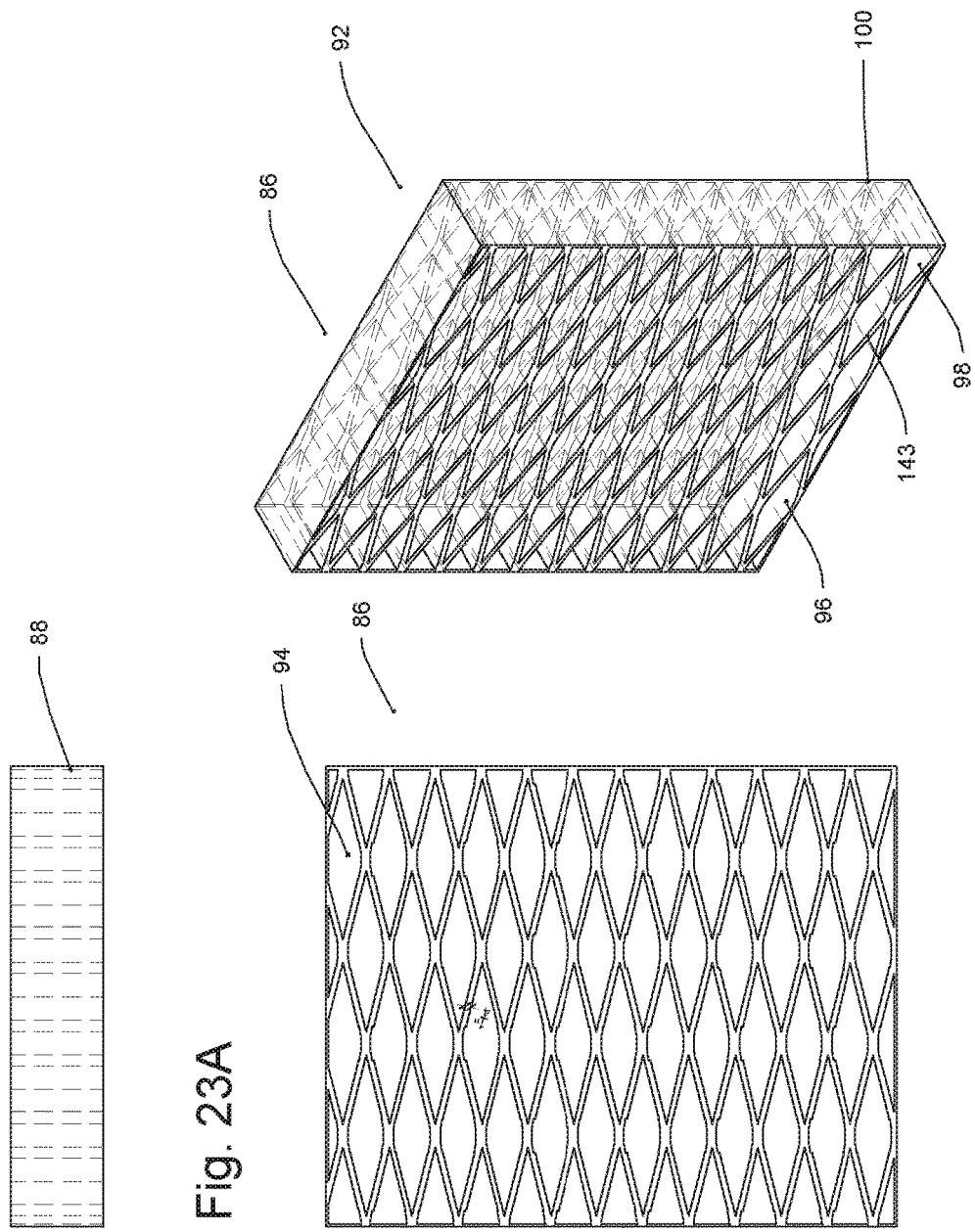

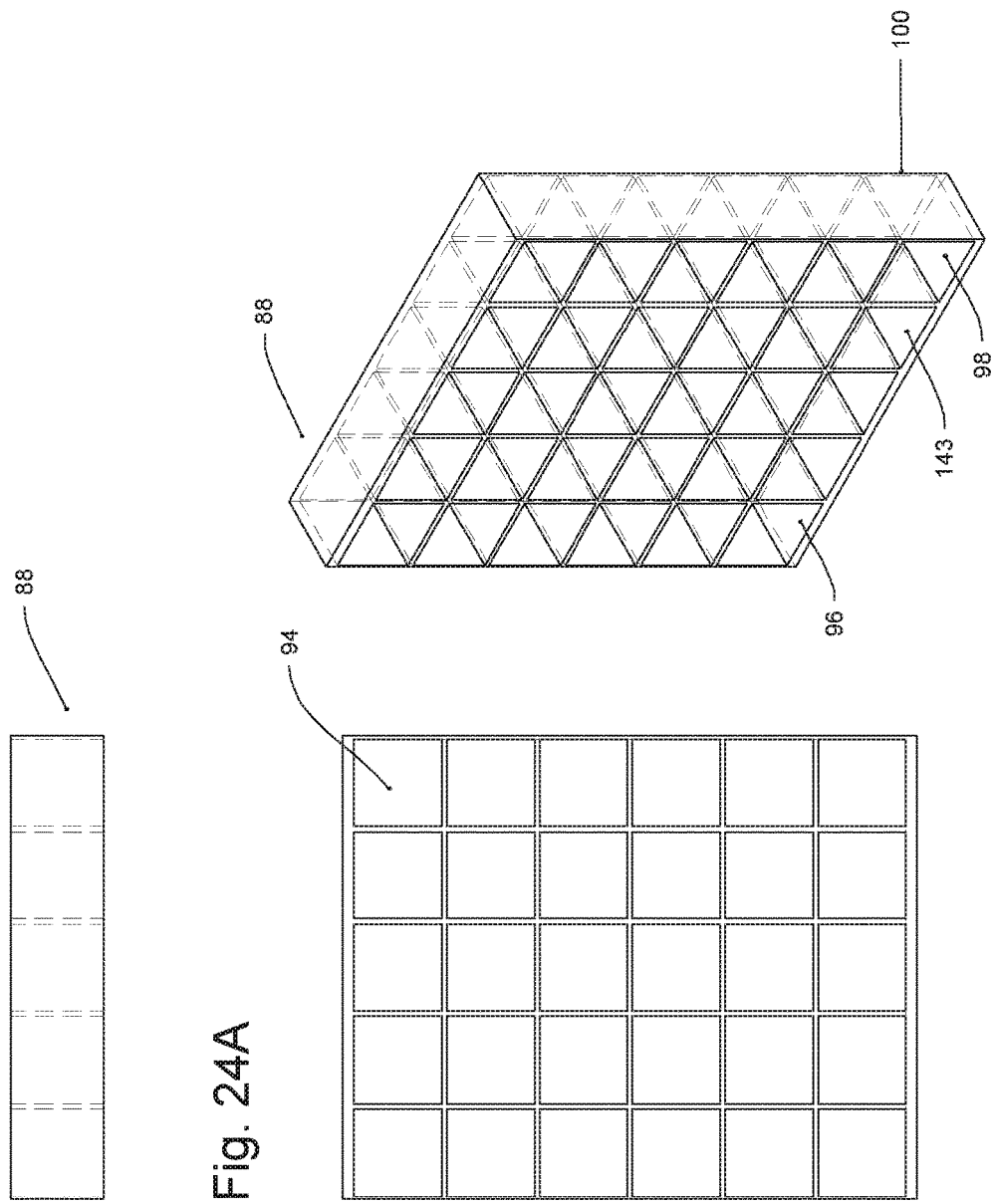

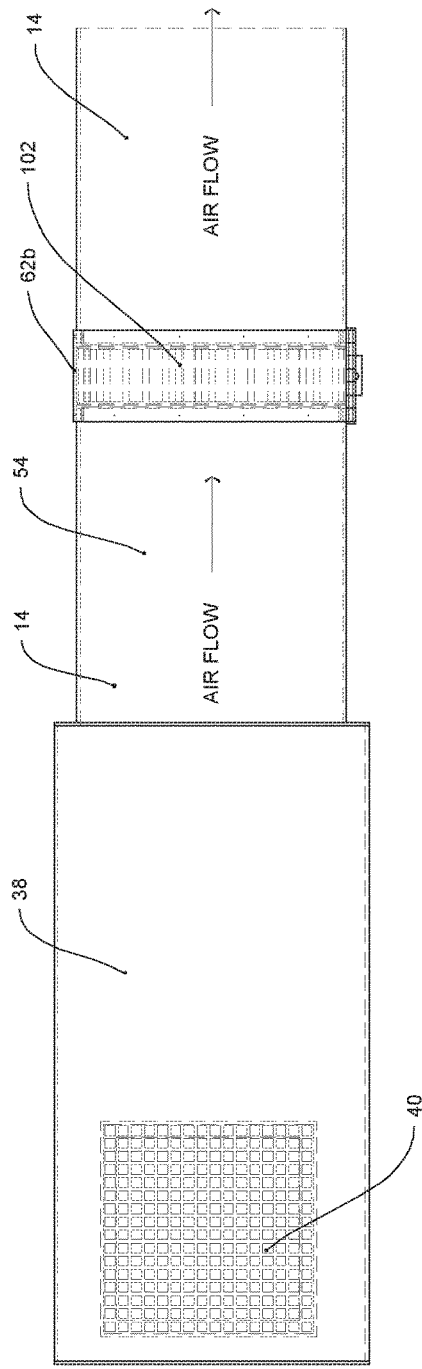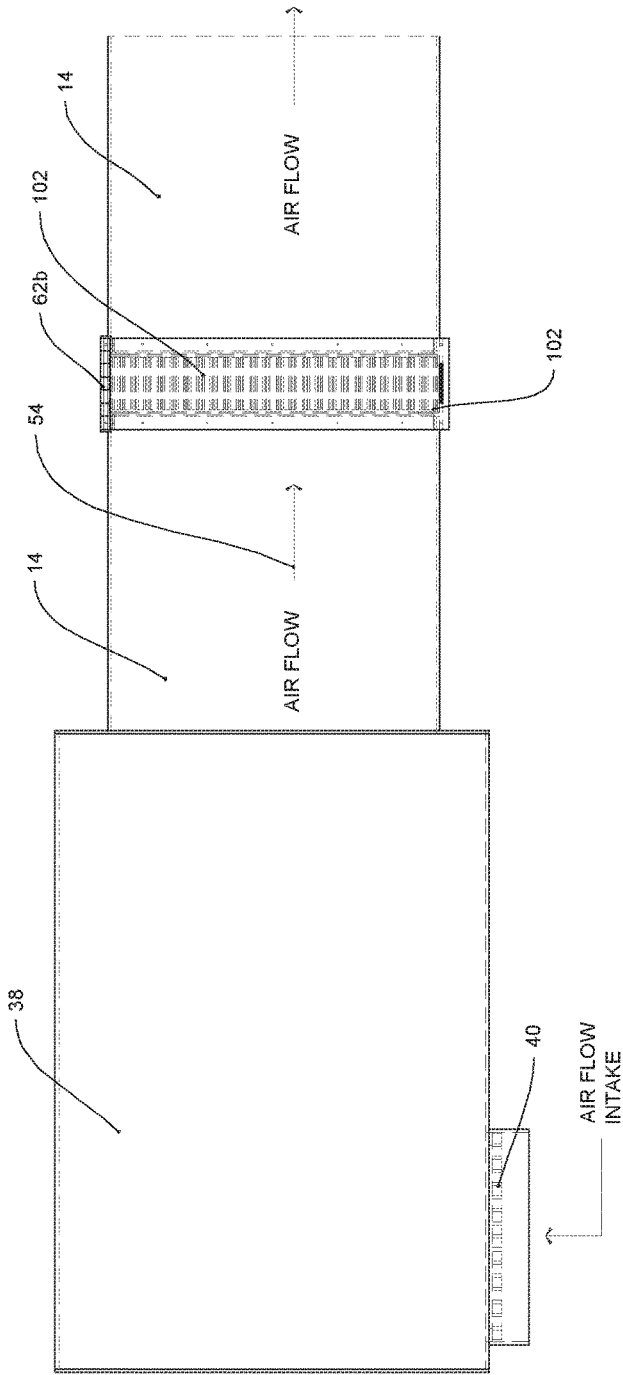

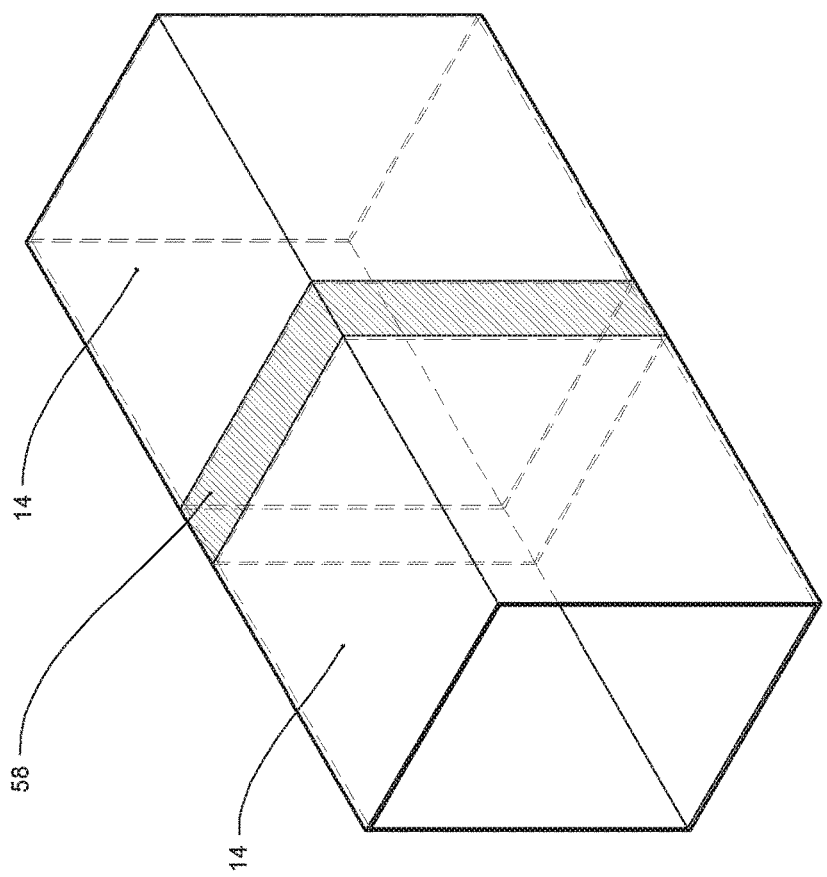

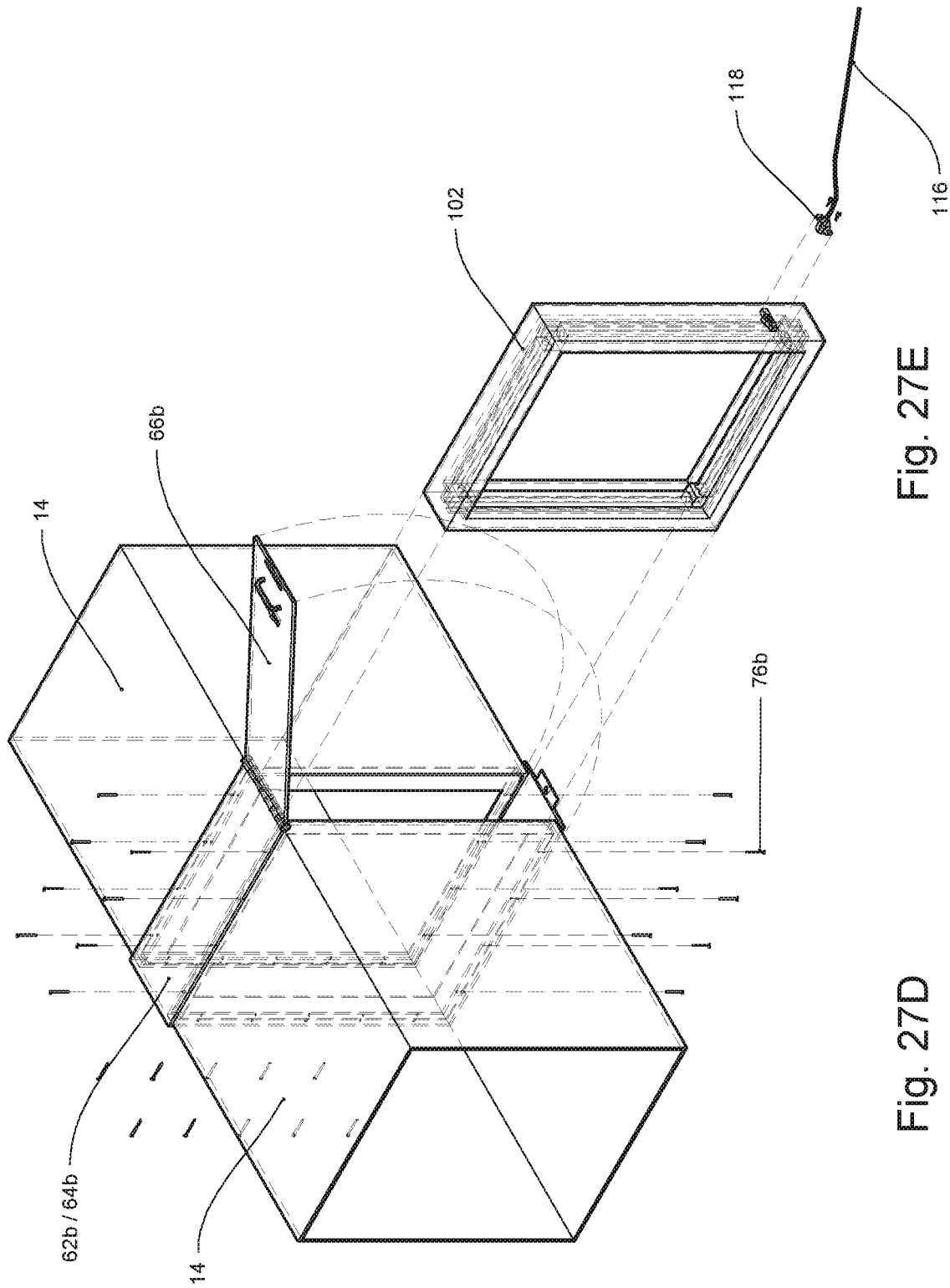

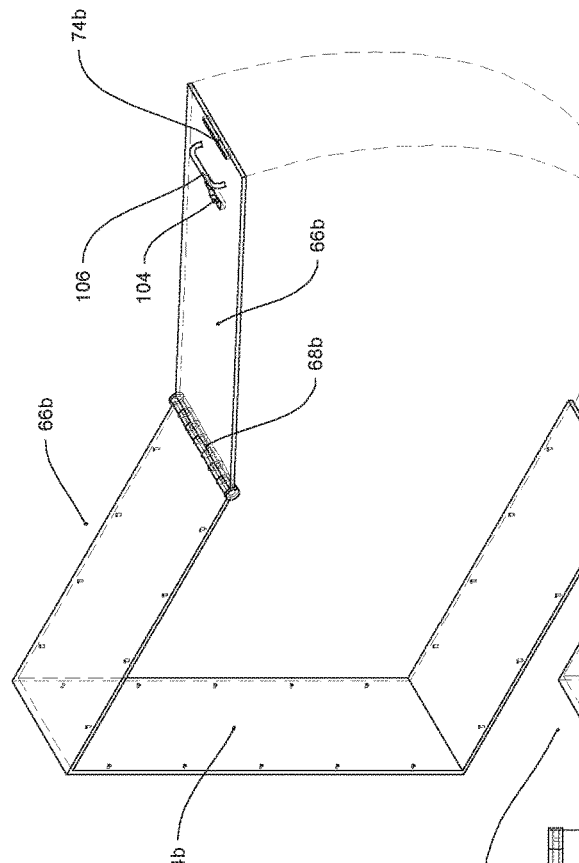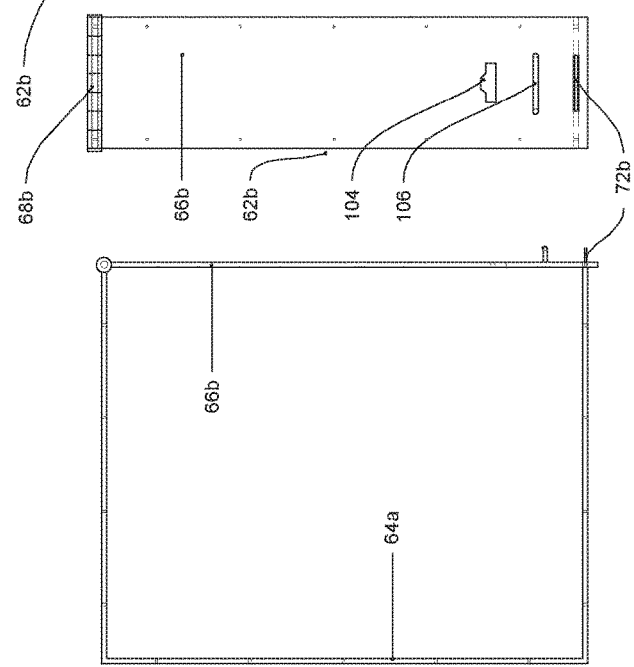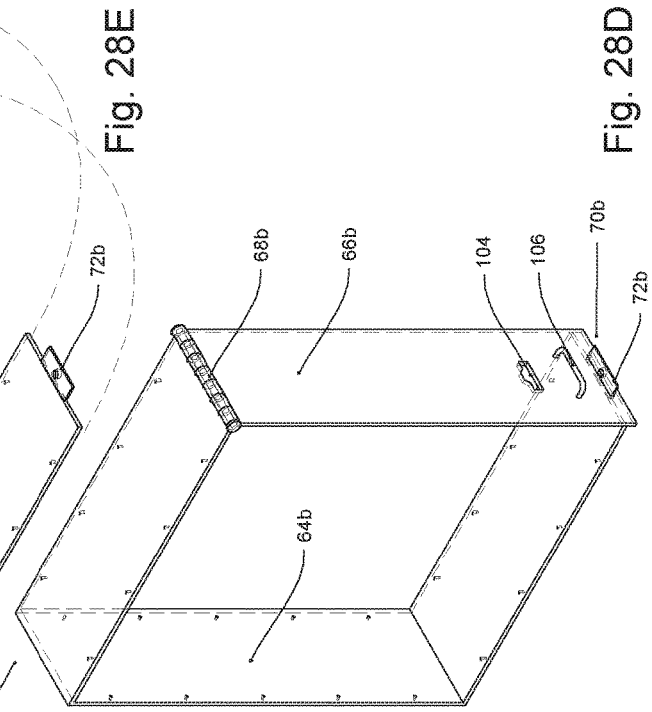

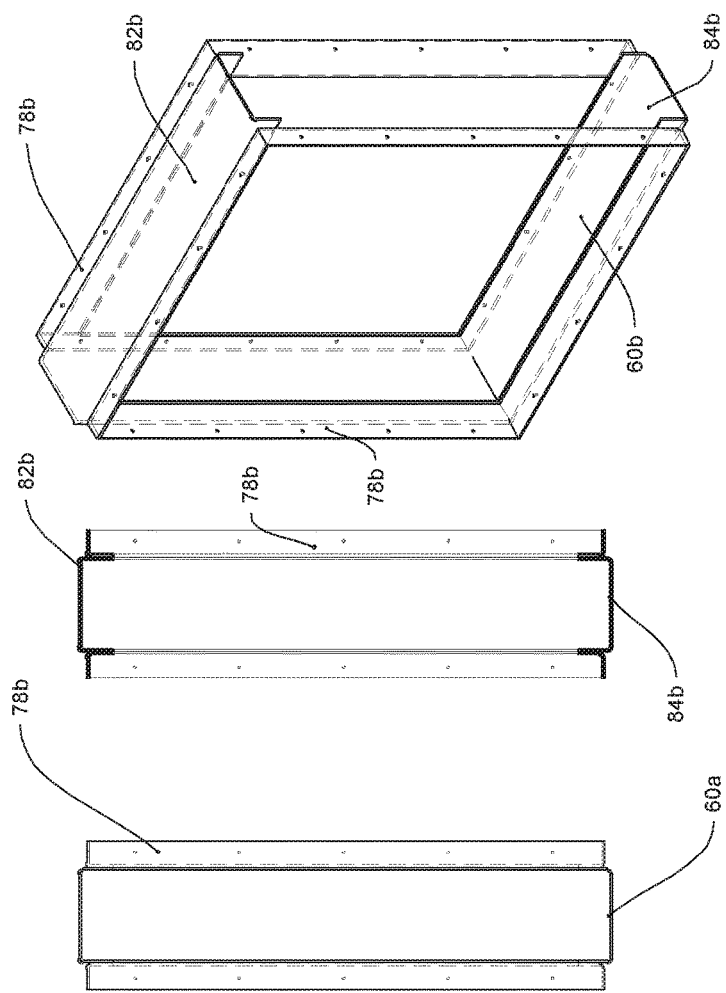
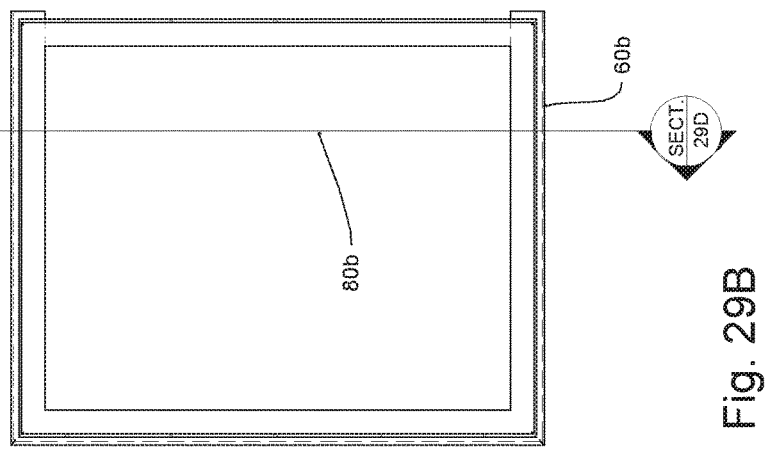
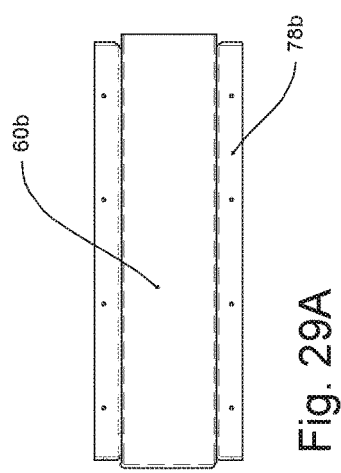

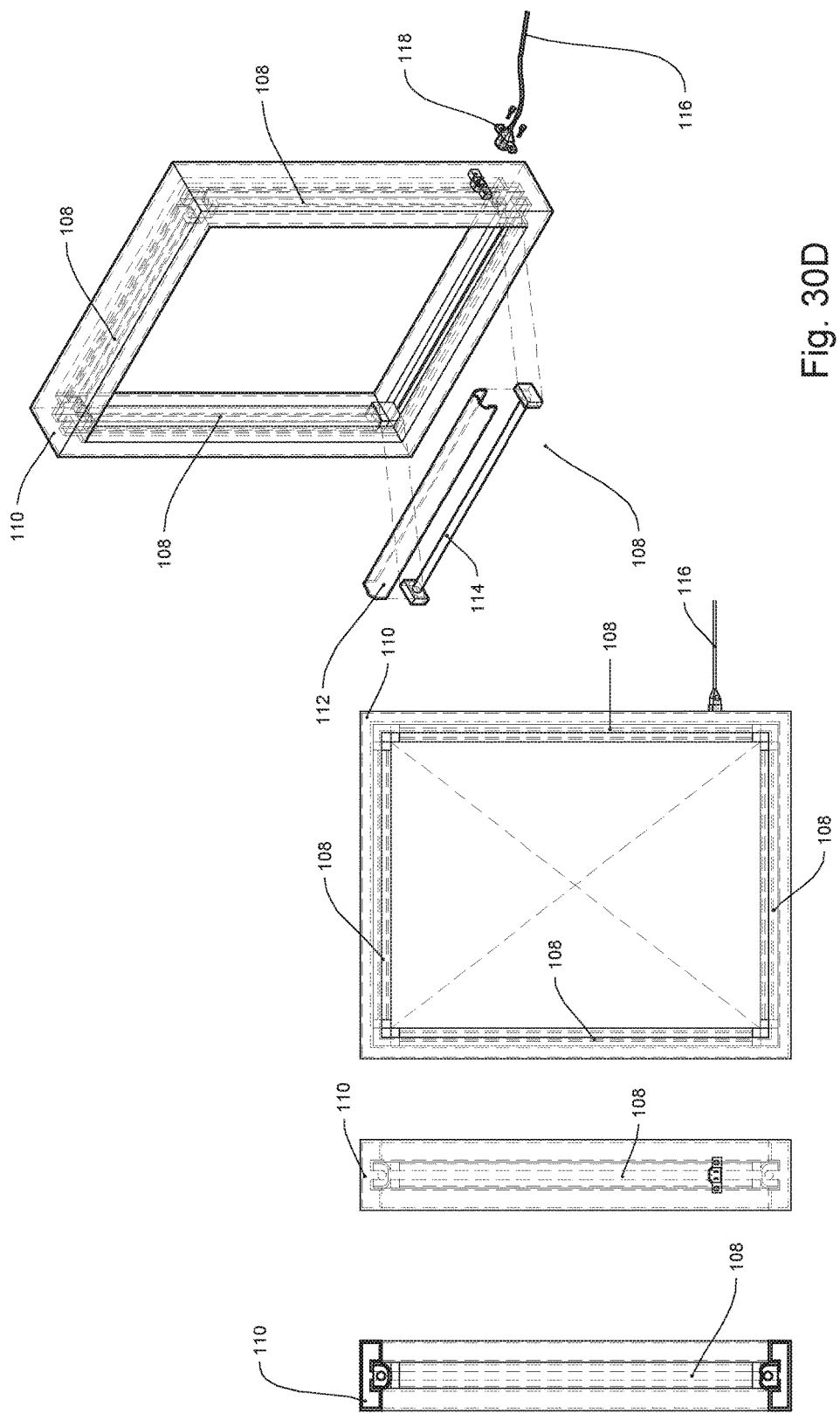

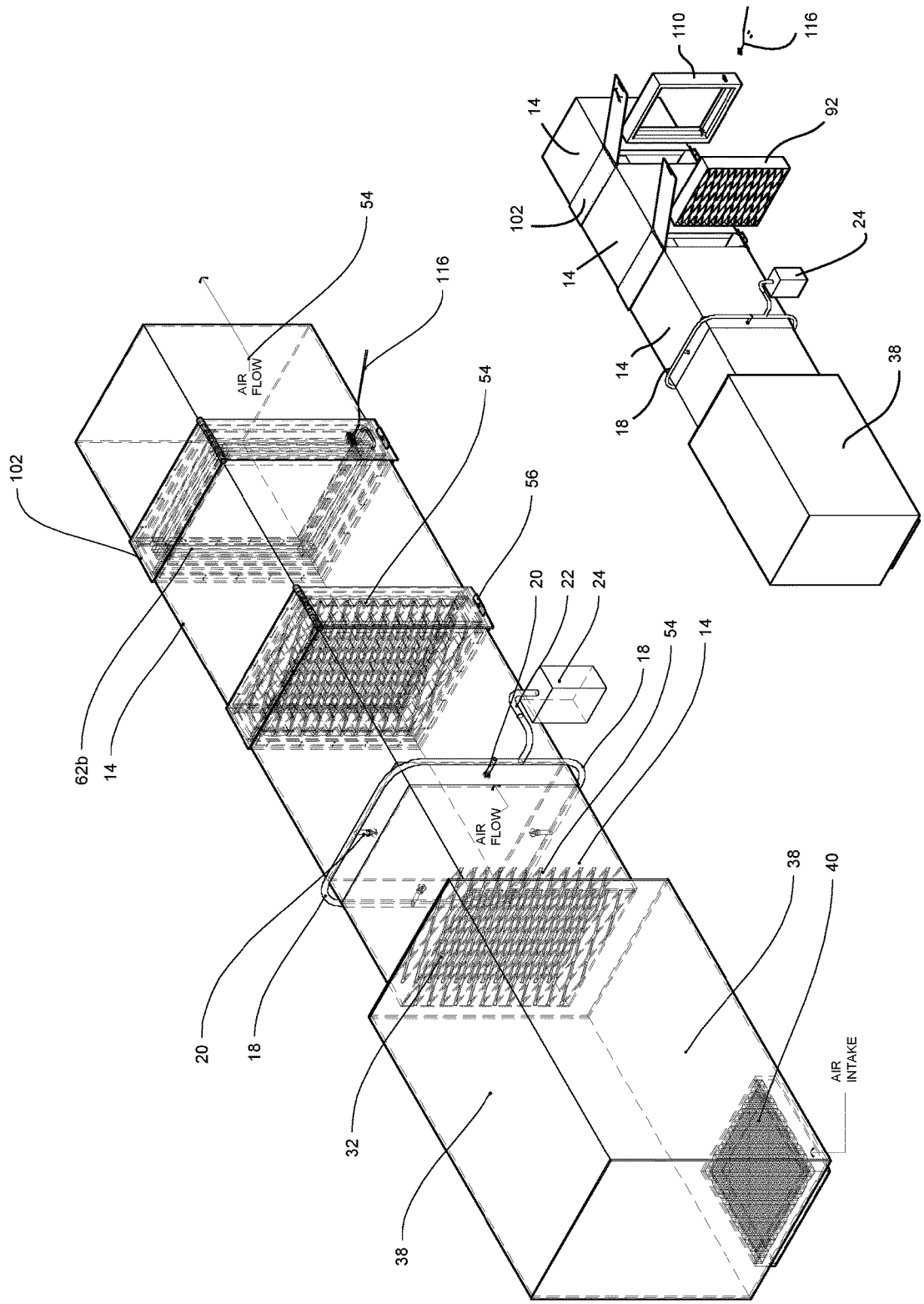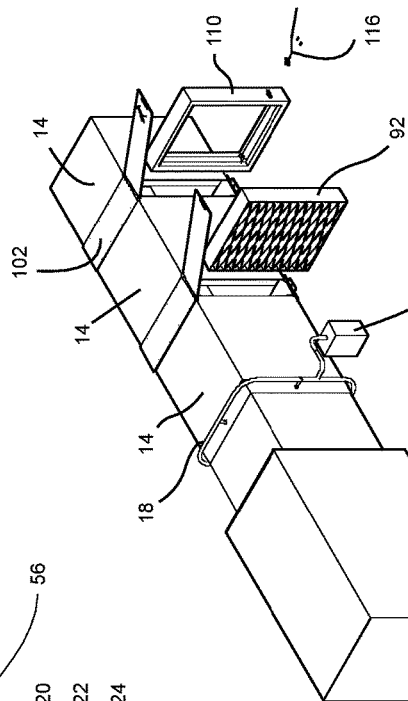

US 11,660,367 B2

AIRBORN PATHOGEN DISENFECTING SYSTEM FOR AN HVAC SYSTEM

FIELD OF THE INVENTION

The present invention relates to an enhanced HVAC system with multiple disinfecting stages.

BACKGROUND OF THE INVENTION

The typical air duct system incorporates a chiller tower and one condenser along with ductwork and a filter. These existing systems were designed to carry hot or cold air to a room. There is no antimicrobial filter or system to kill viruses and bacteria that can slip through the existing filters. People purchase aerosols and spray as needed. Spraying may take care of an immediate problem, however it does not provide prolonged sanitation and is not thorough enough to constantly provide a sanitary product. The aerosol may last for the moment in which it was sprayed but 5 to 10 minutes later it is no longer present in the air.

While vaccines work to help keep people's immunities strong against viruses and other pathogens, each year new viruses enter and spread through the population. When such a spread turns into an event of concern, the implementation of systems to help curb the spread are necessary. While much advancement has been made in filter technology, HVAC systems as a whole are largely unchanged.

Thus, a need in the industry has arisen for air-disinfecting system for HVAC systems is necessary to meet the current demand for increased air quality free or substantially free from airborne pathogens.

SUMMARY OF THE INVENTION

The present invention provides for a system for disinfecting air circulated in an HVAC system. The system includes a multi-phase system, wherein the multi-phase system comprises at least six segments, with at least one segment representing each of at lease one air intake, at least one air handler, and at least one connecting ductwork. The system has at least one interchangeable filter, wherein each filter in said at least one interchangeable filter is an elongate three-dimensional grid with a series of openings to allow circulated are to flow over the air filter's elongate surfaces. The system also has a plurality of ultraviolet lights, and an airborne disinfecting system with at least one spray nozzle mounted to said at least one connecting duct, wherein a supply hose connects said at least one spray nozzle to at least one reservoir of disinfectant.

It is an object of this invention to provide a system capable of killing airborne pathogens.

It is yet further an object of this invention to provide a system that can be easily installed or retrofitted into an existing system.

It is an additional object of this invention to provide modular and replaceable components to the system to allow maximum efficiency in disinfecting the air circulating in and out of the HVAC system.

The above and yet other objects and advantages of the present invention will become apparent from the hereinafter set forth Brief Description of the Drawings, Detailed Description of the Invention and Claims appended herewith.

BRIEF DESCRIPTION OF THE DRAWINGS

FIG. 4 is a front view of the air intake of the system.

FIG. 5A is an exploded view of the disinfecting element of FIG. 5B.

FIG. 6 is an exploded perspective view of the air handler of the system with cent shown in phantom.

FIG. 13 is a perspective view of the air handler of the system shown in FIG. 11 with ductwork.

FIG. 14 is a front elevation view of the air handler system shown in FIG. 13, with filter shown in phantom.

FIG. 15 is a side elevation view of the air handler system shown in FIG. 13.

FIG. 16A is a top view of the replaceable air filter system.

FIG. 16B is a side view of the replaceable air filter system.

FIG. 18D is a perspective view of the engaged mount clamp and door for the replaceable filter system.

FIG. 19A is an embodiment of a filter used with the replaceable filter system shown in FIG. 18D.

FIG. 19B is an embodiment of a filter used with the replaceable filter system shown in FIG. 18D.

FIG. 19C is an embodiment of a filter used with the replaceable filter system shown in FIG. 18D.

FIG. 20A is a top view of the mount clamp and door shown in FIG. 18C.

FIG. 20B is a front view of the mount clamp and door shown in FIG. 18C.

FIG. 20C is a side view of the mount clamp and door shown in FIG. 18C.

FIG. 20D is a perspective view of the mount clamp and door shown in FIG. 18C.

FIG. 20E is a perspective view of the mount clamp and door shown in FIG. 18C, with door shown open.

FIG. 22A is a top view of the filter shown in FIG. 19A.

FIG. 22B is a front view of the filter shown in FIG. 19A.

FIG. 22C is a perspective view of the filter shown in FIG. 19A.

FIG. 23A is a top view of the filter shown in FIG. 19B.

FIG. 23B is a front view of the filter shown in FIG. 19B.

FIG. 23C is a perspective view of the filter shown in FIG. 19B.

FIG. 24A is a top view of the filter shown in FIG. 19C.

FIG. 24B is a front view of the filter shown in FIG. 19C.

FIG. 24C is a perspective view of the filter shown in FIG. 19C.

FIG. 25A is a top view of the interchangeable ultraviolet system.

FIG. 25B is a side view of the interchangeable ultraviolet system.

FIG. 26 is a perspective view of the duct cut for the interchangeable ultraviolet system.

FIG. 27D is a perspective view of the engaged mount clamp and door for the interchangeable ultraviolet system.

FIG. 27E is a perspective view of the interchangeable ultraviolet system used with the mounting frame shown in FIG. 27D.

FIG. 28A is a top view of the mount clamp and door shown in FIG. 27C.

FIG. 28B is a front view of the mount clamp and door shown in FIG. 27C.

FIG. 28C is a side view of the mount clamp and door shown in FIG. 27C.

FIG. 28D is a perspective view of the mount clamp and door shown in FIG. 27C.

FIG. 28E is a perspective view of the mount clamp and door shown in FIG. 27C, with door shown open.

FIG. 29A is a top view of the ultraviolet frame shown in FIG. 27A

FIG. 29B is a front view of the ultraviolet frame shown in FIG. 27A

FIG. 29C is a side view of the ultraviolet frame shown in FIG. 27A

FIG. 29D is a section view of the ultraviolet frame shown in FIG. 27A, taken from A-A shown in FIG. 29B.

FIG. 29E is a perspective view of the ultraviolet frame shown in FIG. 27A.

FIG. 30A is a section view of the replaceable ultraviolet system.

FIG. 30B is a side view of the replaceable ultraviolet system.

FIG. 30C is a front view of the replaceable ultraviolet system.

FIG. 30D is a perspective view of the replaceable ultraviolet system.

FIGS. 32, 33, and 34 are a perspective views of an embodiments of the entire system including ultraviolet system, disinfecting system, and filter system.

DETAILED DESCRIPTION OF THE INVENTION

As described in the background of the invention, the typical air duct system incorporates a chiller tower and one condenser along with ductwork and a filter. These existing systems were designed to carry hot or cold air to a room. There is no antimicrobial filter or system to kill viruses and bacteria that can slip through the existing filters. People purchase aerosols and spray as needed. Spraying may take care of an immediate problem, however it does not provide prolonged sanitation and is not thorough enough to constantly provide a sanitary product. The aerosol may last for the moment in which it was sprayed but 5 to 10 minutes later it is no longer present in the air.

The present invention provides a multi-stage and multi-component disinfecting system for an HVAC system 10, which solves the long felt need for a thorough and reliable system of disinfecting the air in an HVAC system.

Figure 32:
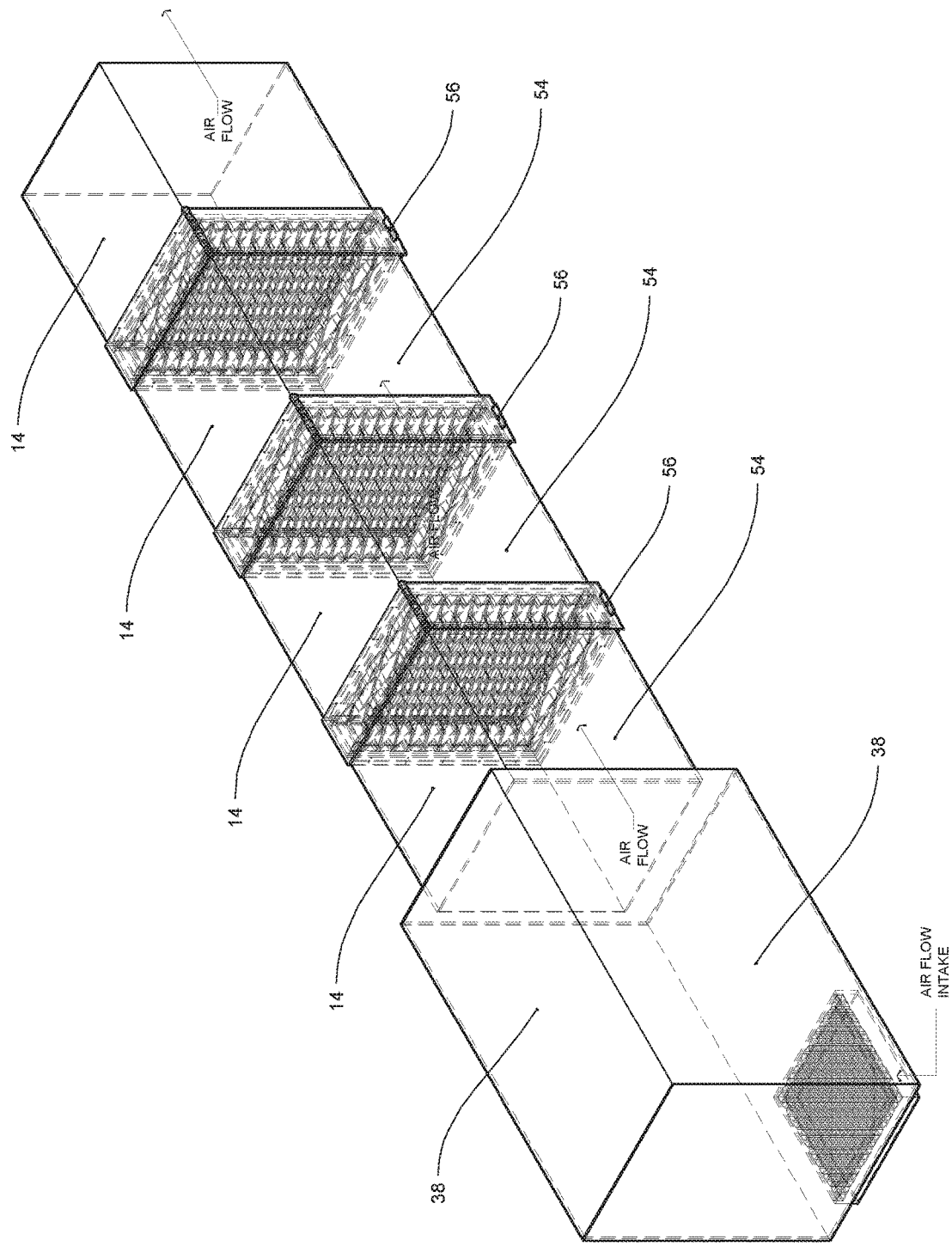

The system primarily operates with six stages, as may be seen in FIGS. 32, 33, and 34. In the first stage 40, untreated air enters in to the return 40 for the HVAC system 10. The air then travels through the second stage 15, which is an ultraviolet treatment area. At this point the air is mostly disinfected and then passes through the third stage 38, which is the air handler 38 of the system. After passing through the air handler 38, it is necessary to decontaminate any residual pathogens left in the air, which may have accumulated from surfaces in the HVAC system. The fourth stage 102 is an additional ultraviolet treatment area, as shown Primarily in FIGS. 25A-27D, and FIGS. 30A-31C. The fifth stage 35 is a disinfecting area, which can be either a spray or mist system 36 with disinfectant solution, shown primarily in FIGS. 1-15, or a solid filter 32, dipped in liquid disinfectant and left to dry, as shown primarily in FIGS. 6, 8, 16A-16C, 19A-19C, and 22A-24C. In some embodiments, both a liquid spray or mist system 36 and a dry solid filter 32 are used, as may be appreciated from FIG. 6. Once it passes through this disinfecting stage 35, the air passes to its final stage 13, flowing through the system supply 13.

Also shown in FIGS. 1-15 are the intake filter vent 26, vent frame 28, and vent grill 30, the disinfecting filter mounting frame 34, and air return filter.

Because HVAC systems in buildings may be complex, and replacing said systems could be an issue, this invention allows for an easy retrofit. Each component is easily adaptable for use with an existing system. For example, a cut in the ductwork can be made to allow the stainless steel frame 60a enclosing a filter 32 to be inserted, wherein the frame housing 62a/62b is contoured to match the profile of the existing ductwork 14. Once this frame 60a is inserted, the filters 32 can be interchanged, refreshed, or replaced as necessary. The filters 32 can also be systematically sprayed by spray nozzles 20, as may be seen in FIGS. 6 and 8, with disinfectant to continuously keep a layer of disinfecting material on said filter 32.

Figure 1:
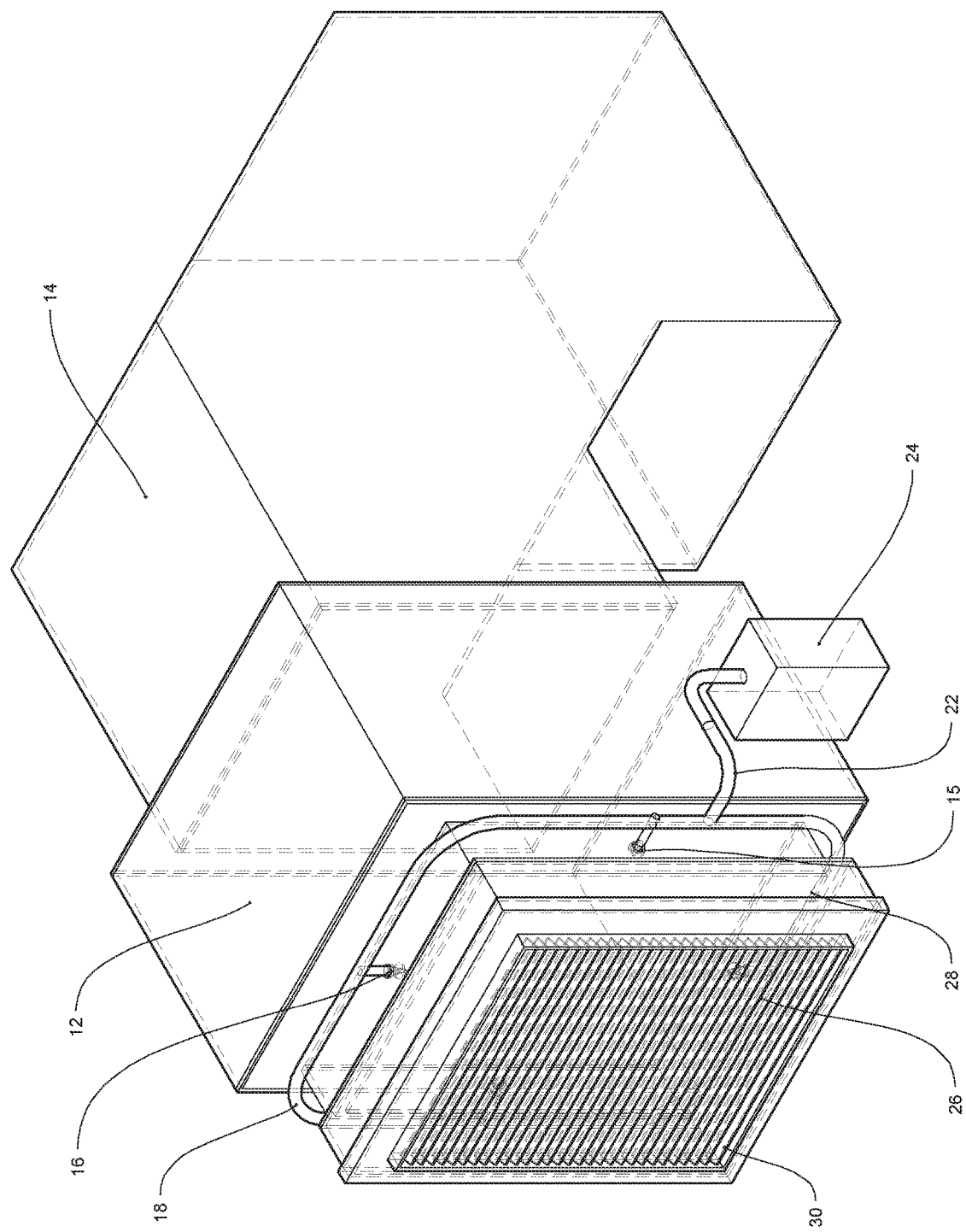
FIG. 1 is a perspective view of an air intake of the system.
Figure 2:
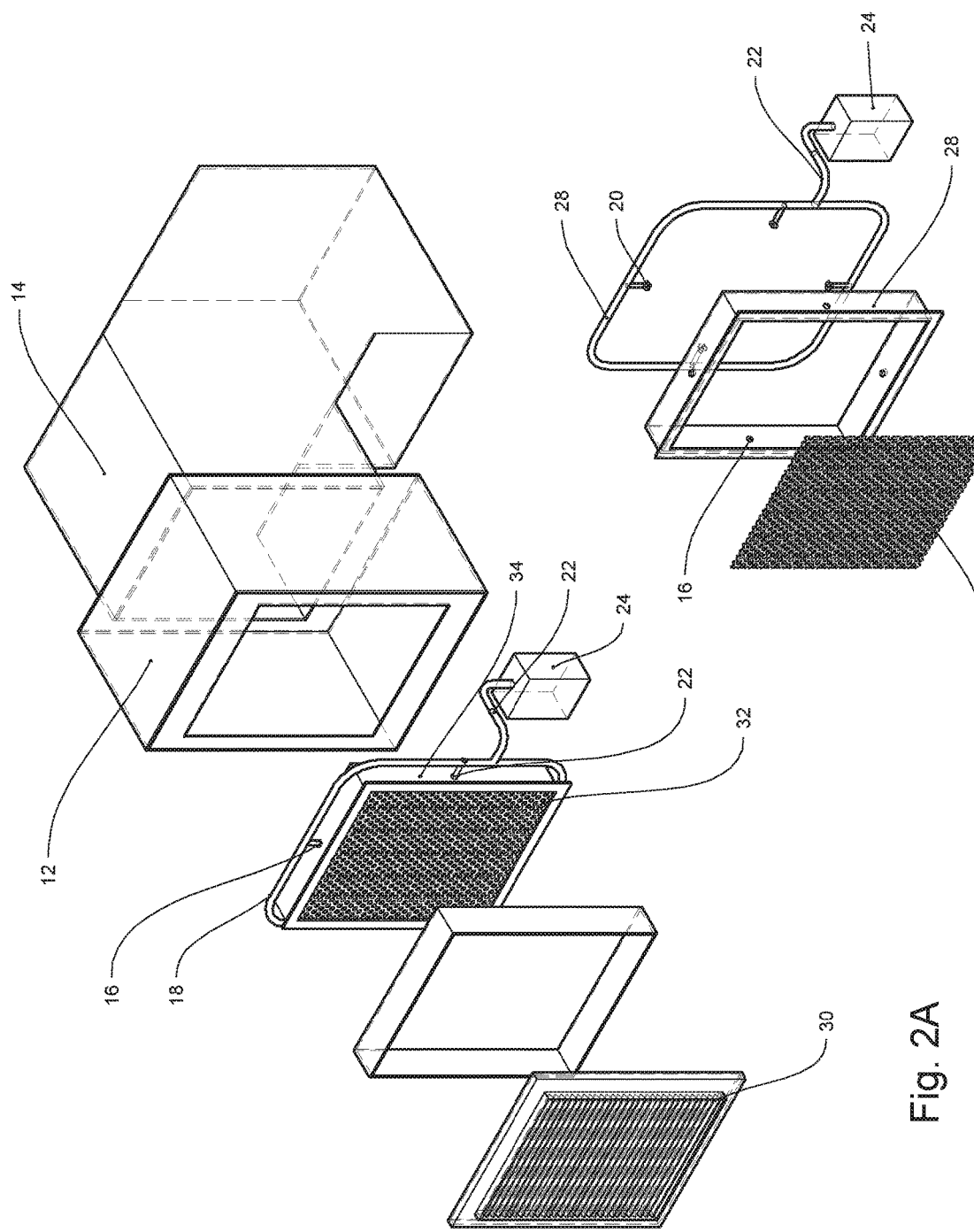
FIG. 2A is an exploded view of perspective view of FIG. 1.
FIG. 2B is an exploded view of the disinfecting element of FIG. 2A.
Figure 3:
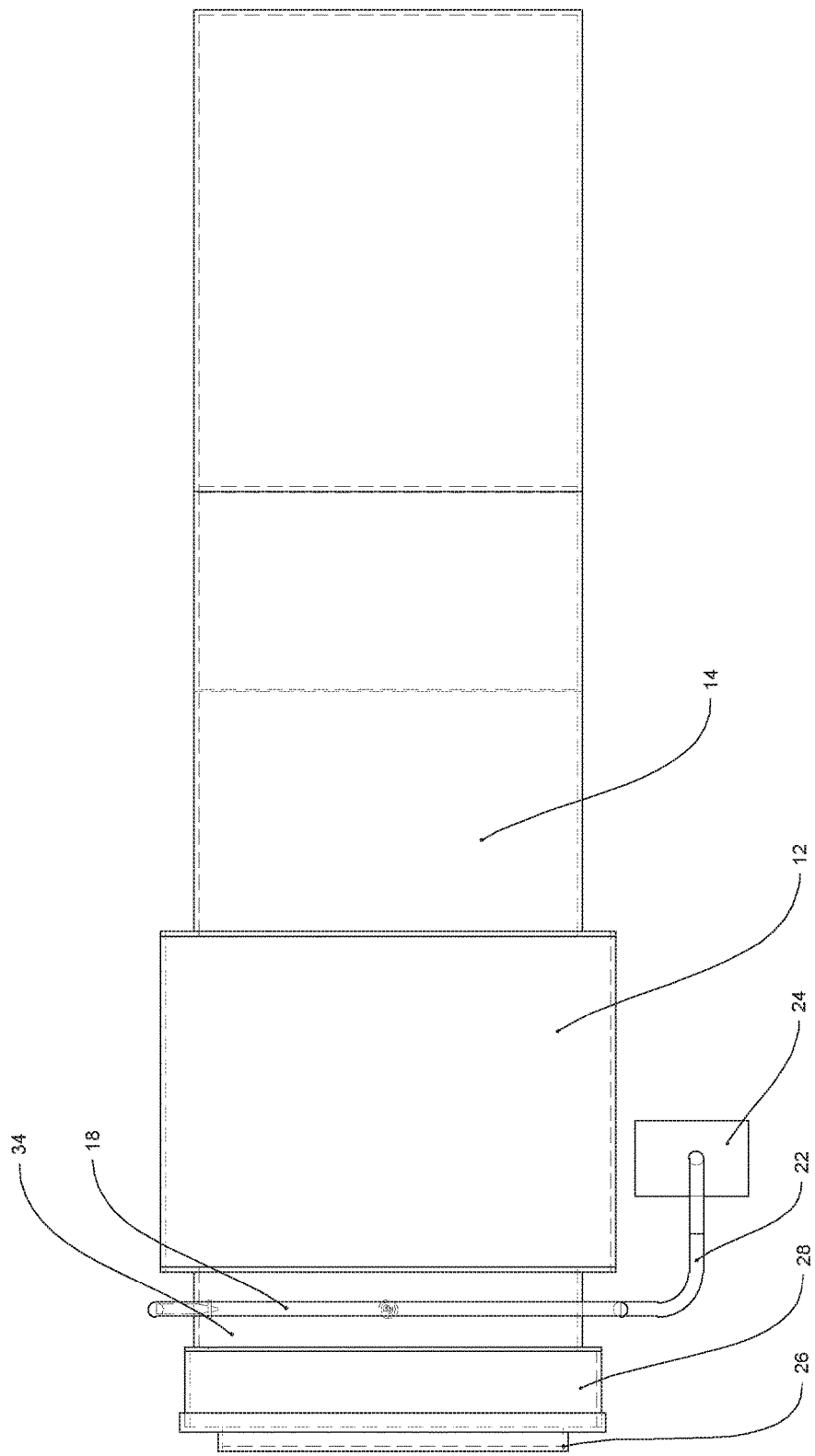
FIG. 3 Is a top view of the air intake of the system.
Figure 5B:
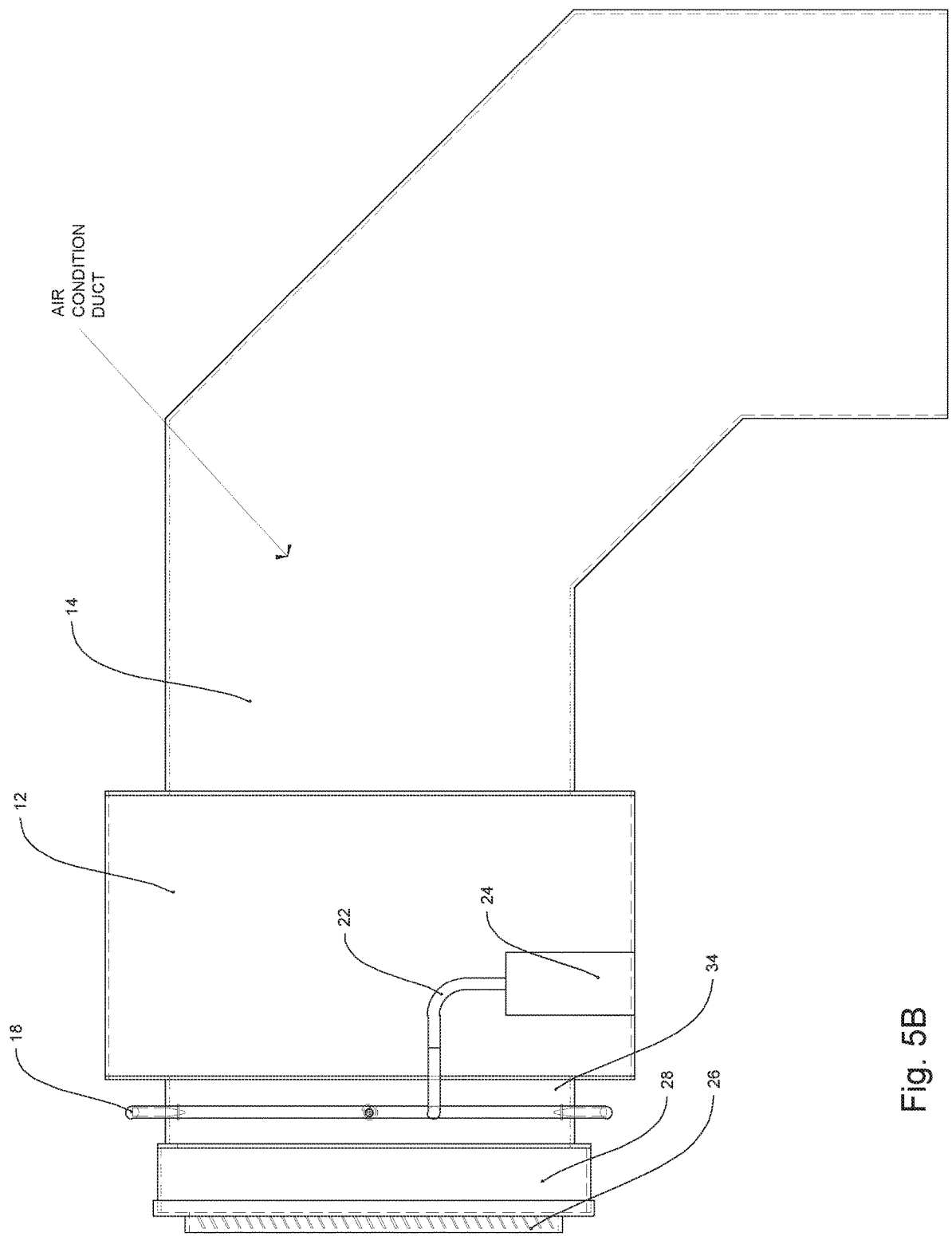
FIG. 5B is a side view of the air intake of the system.
Figure 7:
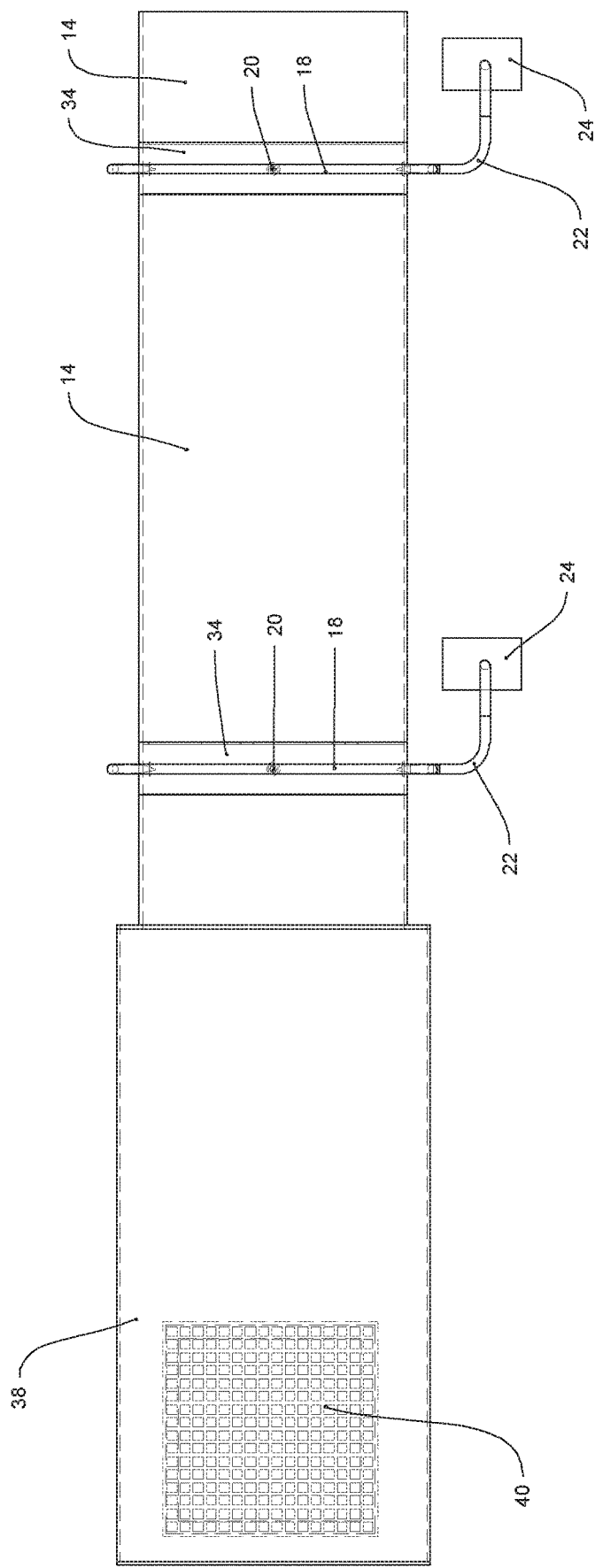
FIG. 7 is a top view of the air handler of the system with vent shown in phantom.
Figure 8:
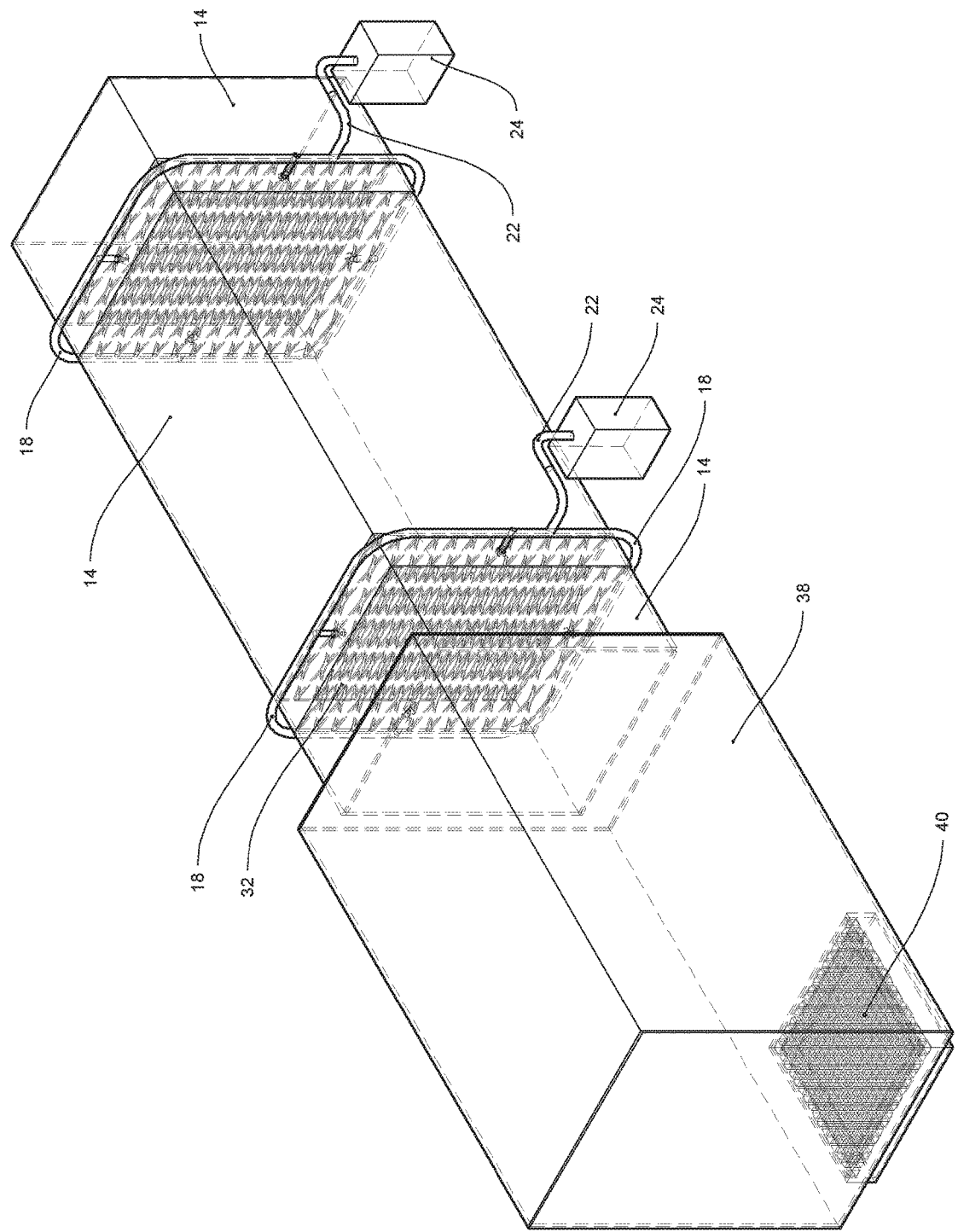
FIG. 8 is a perspective view of the air handler of the system with components shown in phantom.
Figure 9:
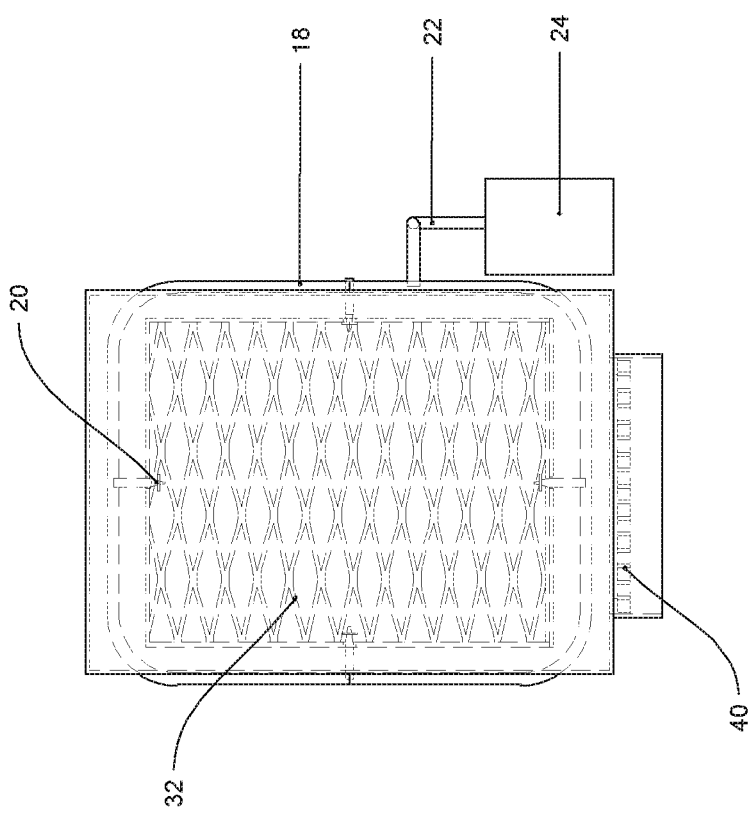
FIG. 9 is a front elevation view of the air handler of the system.
Figure 10:
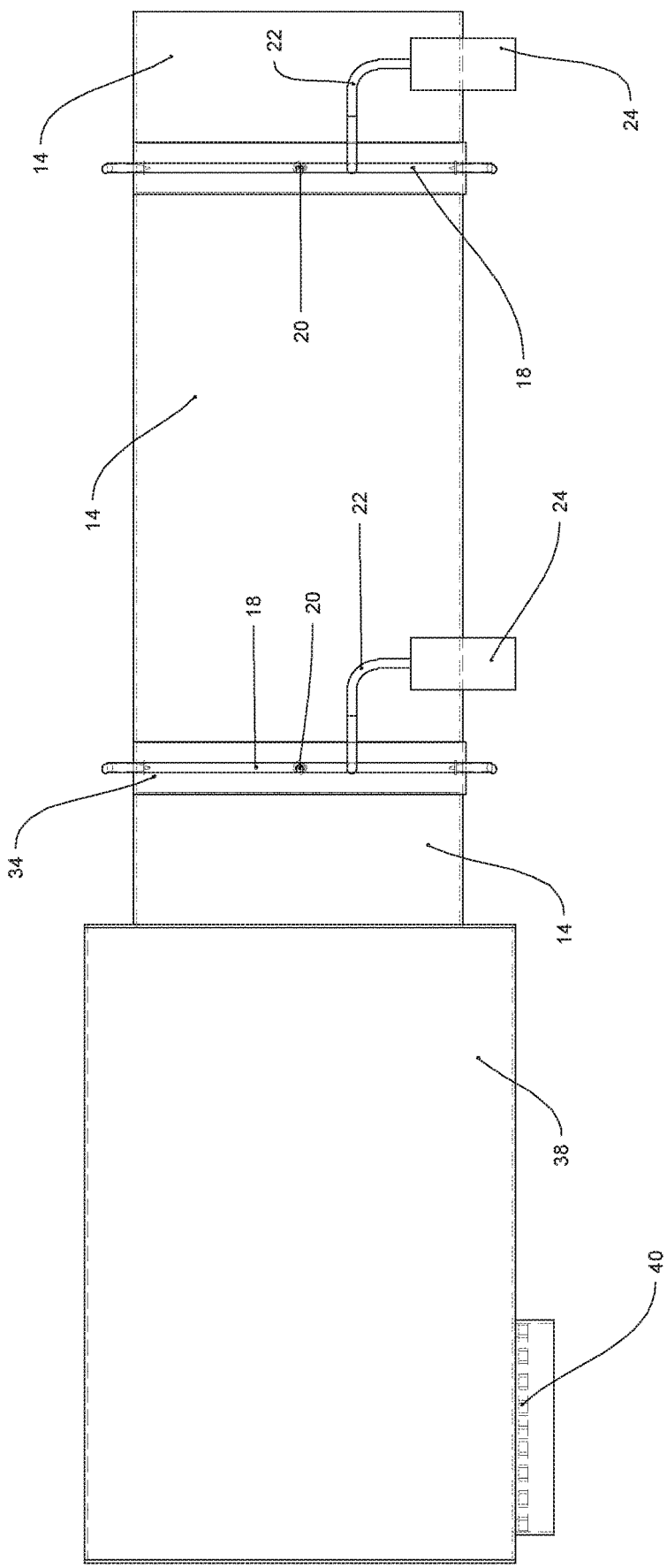
FIG. 10 is a side elevation of the air handler of the system.
Figure 11:
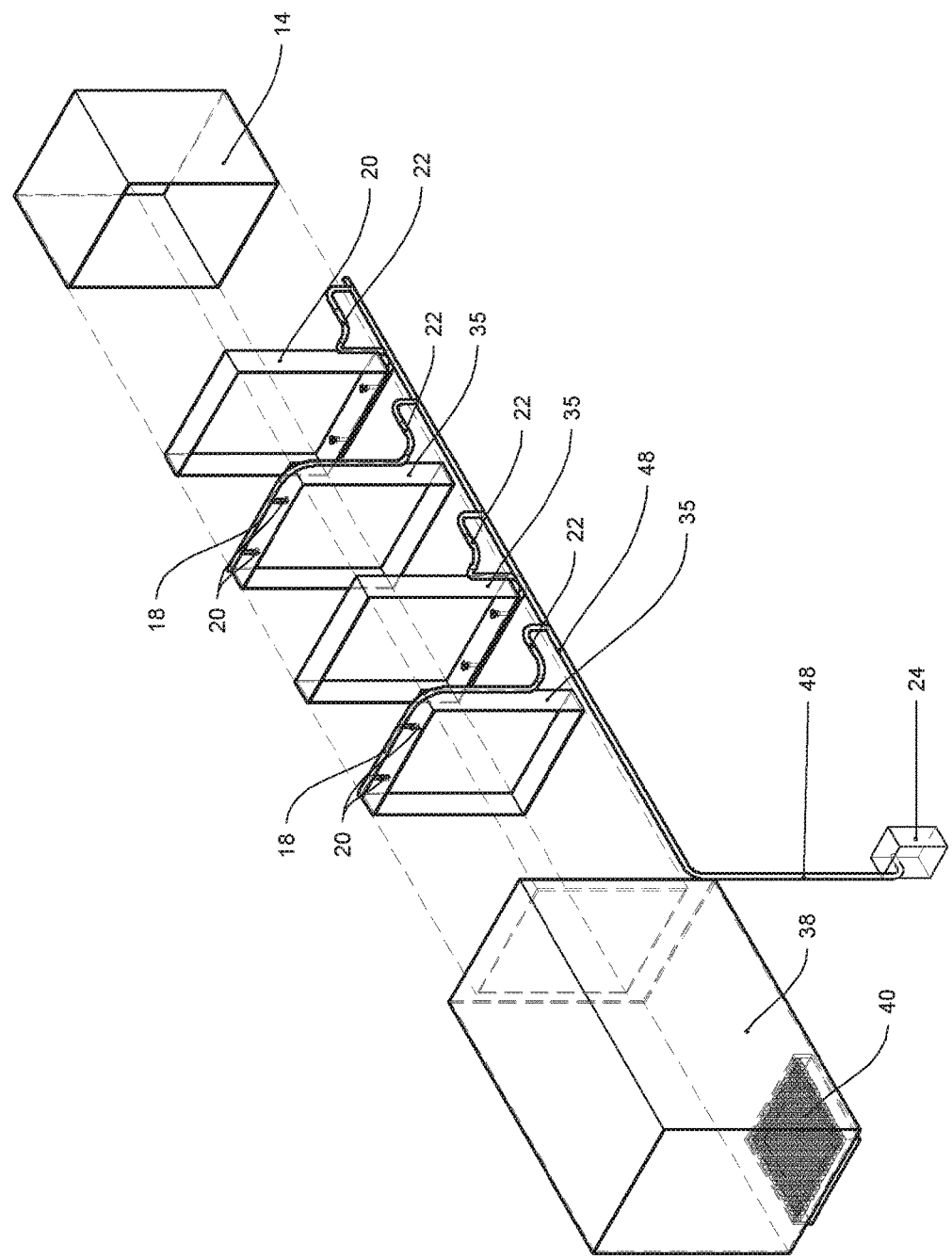
FIG. 11 is a perspective view of the air handler of the system with a centralized sanitizer system with satellite spray nozzles.
Figure 12:
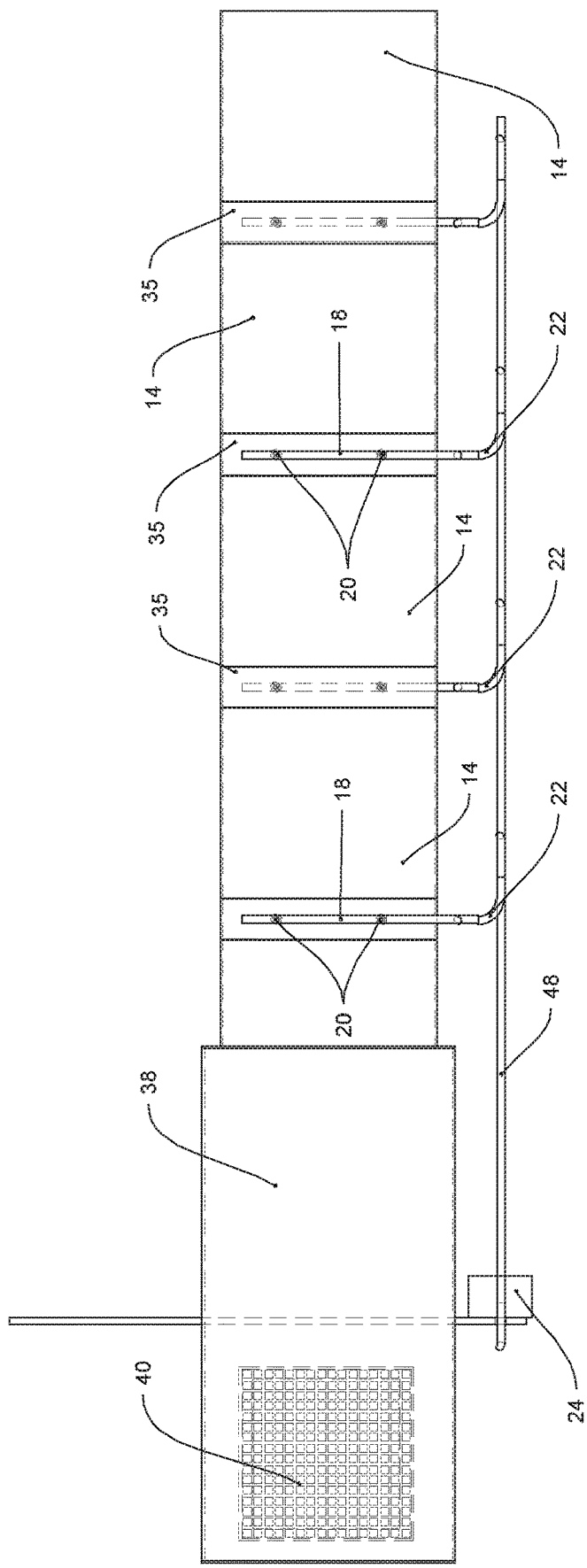
FIG. 12 is a top view of the air handler shown in FIG. 13, with vent shown in phantom.

Spray nozzles 20 are inserted in to the ductwork 14. The hose 18/22 for the spray system nozzles 20 can be installed on the interior of existing AC ductwork 14, or on its exterior with penetrations 16 in to the ducts 14 for inserting these nozzles 20. A rubber airtight sleeve is used when penetrating the duct 14 to provide an aperture 16 for the nozzle 20 spray system 36. The nozzles 20 may be pointed at the filters 32 to keep a continuous layer of disinfecting material on the filter 32, or may be positioned to create a spray or mist that decontaminates the air directly, as shown in FIGS. 10 and 11. A reservoir 24/44/46 can be located either locally near the spray nozzles 24 above a drop ceiling 50, as may be seen in FIGS. 6, 7, 8, and 10, or centrally contained in a reservoir 44 near the HVAC equipment in a utility closet, as shown in FIGS. 11-15. These reservoirs 24/44/46 are ideally refillable, however, there may be instances where the reservoirs 24/44/46 are prefilled replaceable containers that are swapped out when empty. Mechanical pumps will be used to inject disinfectant through the spray nozzle 20, and can similarly be centrally located in the HVAC utility closet, or a plurality can be spread out to key areas of the duct work, allowing targeted disinfecting with pumps being individually programmed or automated.

Also shown in FIGS. 11-17 are the wall 52, a path of airflow 54, a replaceable filter segment 56, and a duct cut 58.

Automation is a key element to this system. Prior to this invention, an occupant of an area needs to physically disinfect an area by using a spray bottle, but this does not monitor the current conditions. This system will ideally be used with a programmable interface that is wirelessly enabled, such as Wi-Fi or Bluetooth enabled. A control module may be set, like a timer, or may be programmed to automate the system based on time of day, day of the week, based on occupancy, or randomized for efficiency. The system allows for both automation and control, wherein the automated system will monitor current conditions and initiate disinfecting as necessary, whereas control would allow a user to initiate the program whenever said user feels it necessary to activate the disinfecting system. This operability allows for maximum flexibility for a controlled disinfecting.

Further, ultraviolet lamps 108 are included for disinfecting. Similar to inserting a filter 32, a segment of ducting is cut from the existing ductwork 14. Therein, a stainless steel frame 62b is inserted in to a frame housing 64b, formed to match the contour of the duct 14, as may be seen in FIGS. 27A-31C. There, interchangeable ultraviolet lamps 108 mounted to a steel frame 110 may be inserted. The lamps 108 can be calibrated for the intensity needed to kill any pathogens, or reduce them by a desired number. The system can include a single bulb 114, or a plurality of bulbs 108 as necessary. As may be seen in FIGS. 30A-30D, an array of ultraviolet lights 108 are mounted to the steel frame 110. Each light 114 in the array of ultraviolet lights contains a bulb 114, and glass covering 112.

This system may have multiple configurations, or a combination of some or all configurations. A first configuration includes a metal frame 60a with removable filter 32 and sanitary injection HVAC feed 18 with spray nozzles 20. In the first configuration, the existing HVAC is separated at several points along the trunk line of the A/C duct 14. A frame 60a and frame housing 62a are inserted between two ducts 14. On the frame 60a there is a protrusion that is trained on the center of the A/C duct 14. At the end of the protrusion is the spray nozzle 20. A hose 18 connects the stem of the nozzle 20 to a supply hose 22/48 to a reservoir 24/44/46 of disinfectant. At timed intervals, a spray will be emitted directly into the main trunk line to sanitize the air circulating through the ducts 14. The filter 32 will be removed and replaced as needed. For sensitive areas the filter will require replacement more often. With several installments throughout the A/C ductwork, the sprays can either be simultaneously or programmed to work independent of each other.

In a second configuration, with multiple penetrations 16 throughout ductwork 14, a frame-less installation is used with multiple penetration points 16 along the A/C duct system. These penetrations 16 will be sized for spray nozzles 20 spaced out periodically through A/C ductwork 14. The nozzles will be emitting the disinfectant starting with higher concentrations at the beginning of the line and then reducing concentrations down the line. This system can be programmed to release at once or systematically down the trunk of the duct. The purpose of the spray is to mix with contaminated air, purifying it and then supplying it back to the building.

Figure 16C:
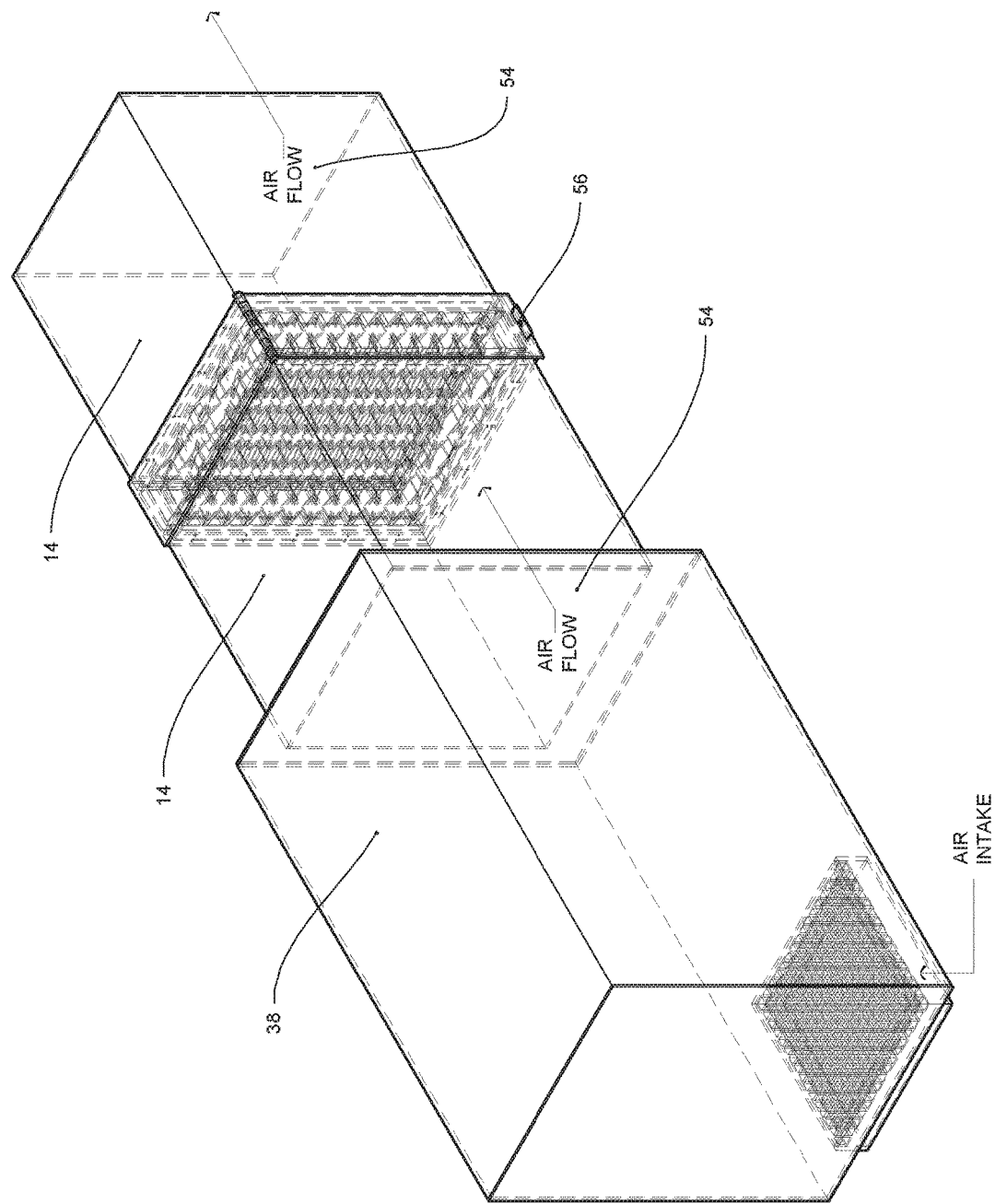
FIG. 16C is a perspective view of the replaceable air filter system.
Figure 17:
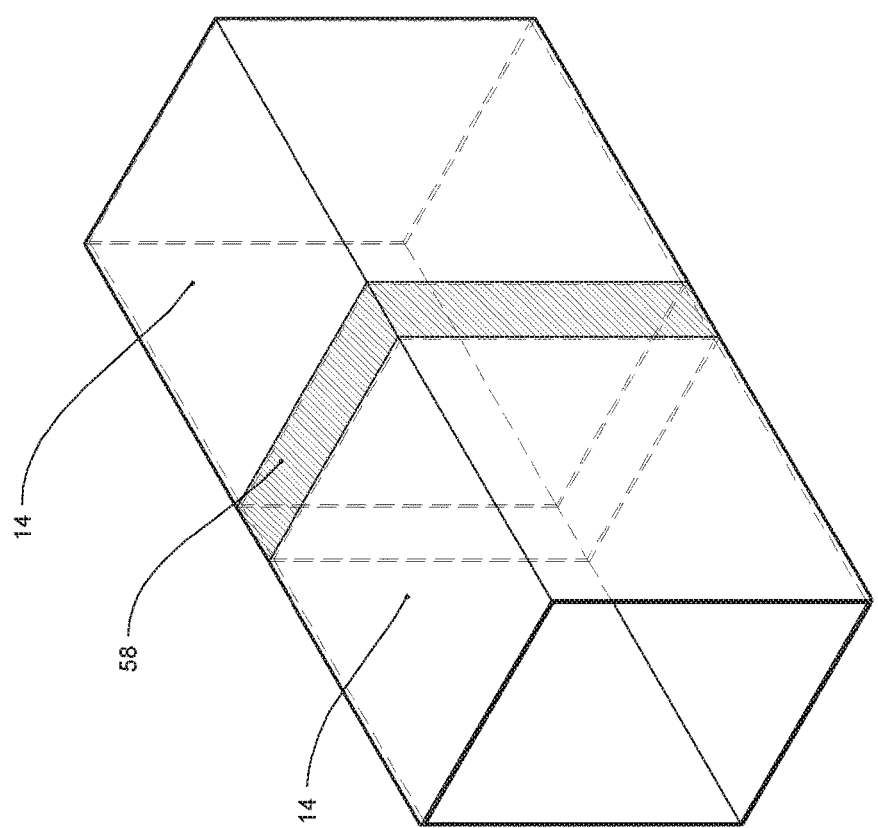
FIG. 17 is a perspective view of the duct cut for the replaceable air filter system.
Figure 18B:
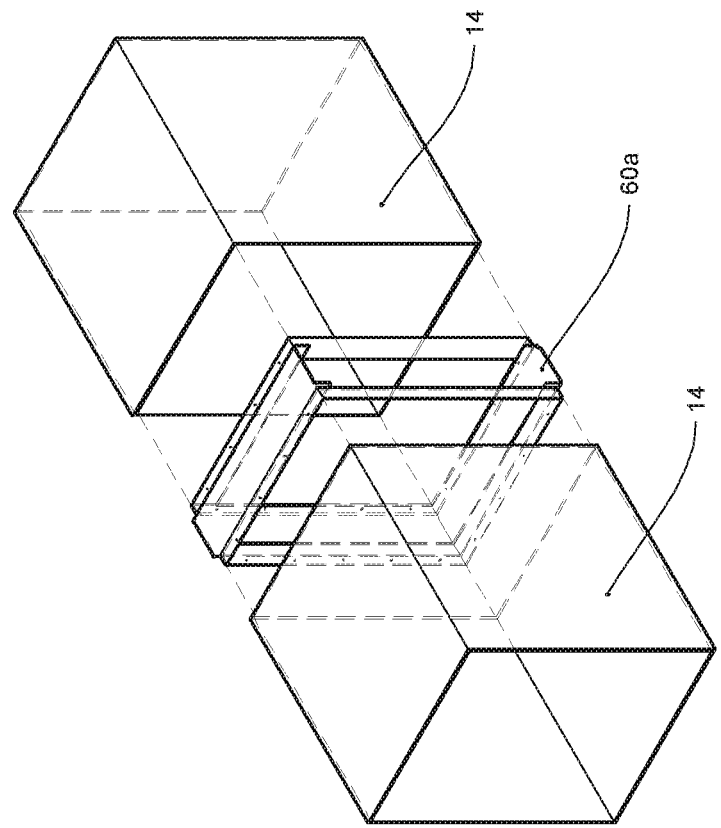
FIG. 18B is a perspective view of the mounted filter frame for the replaceable air filter system.
Figure 18A:
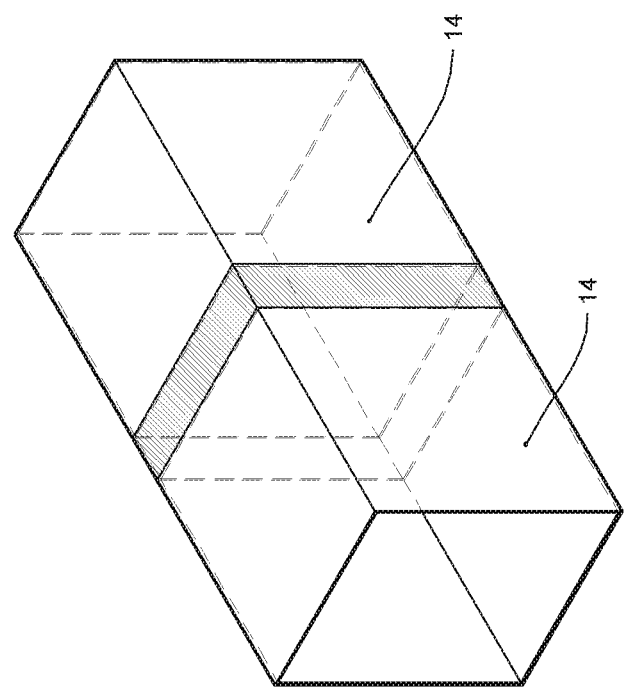
FIG. 18A is a perspective view of the mounting for the filter frame for the replaceable air filter system.
Figure 18C:
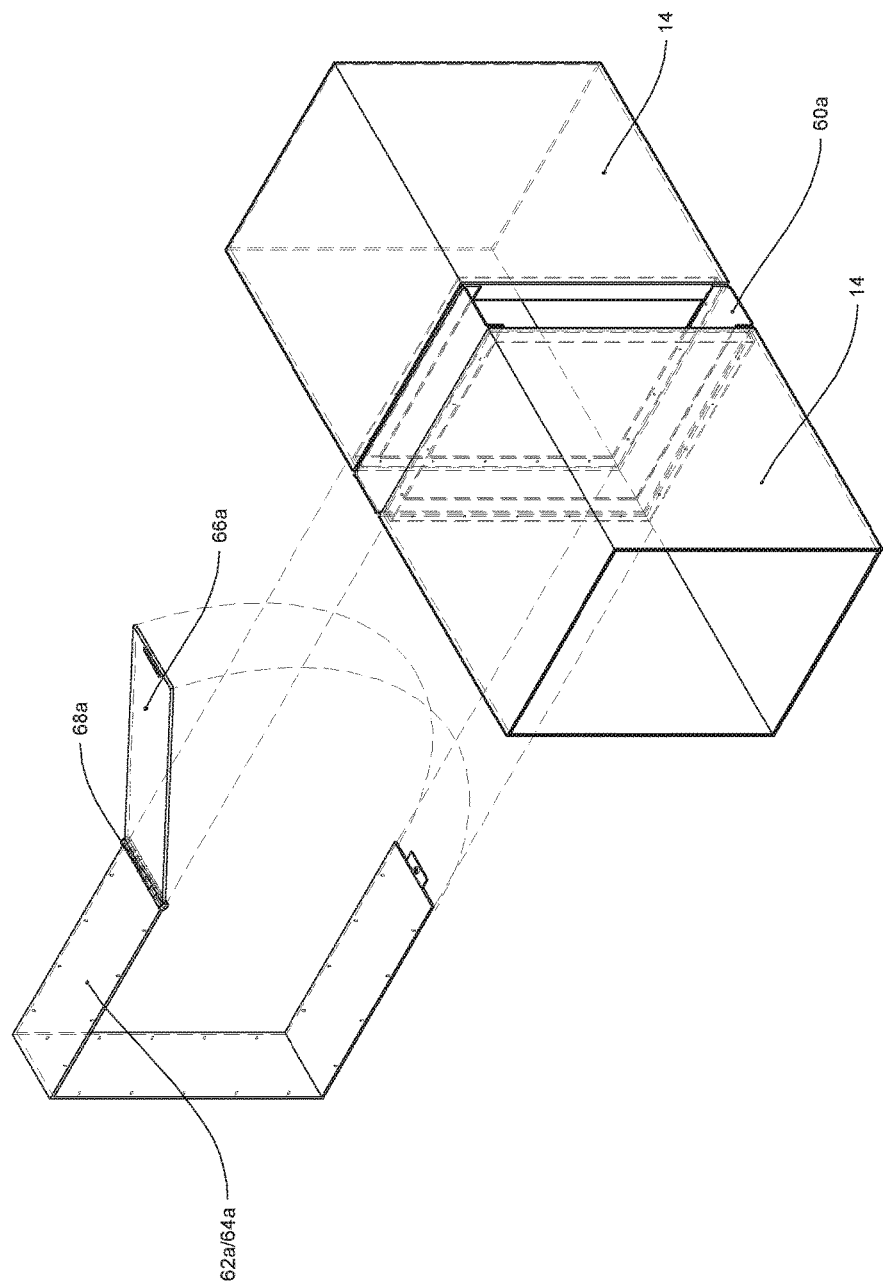
FIG. 18C is a perspective view of the disengaged mount clamp and door for the replaceable filter system.
Figure 21E:
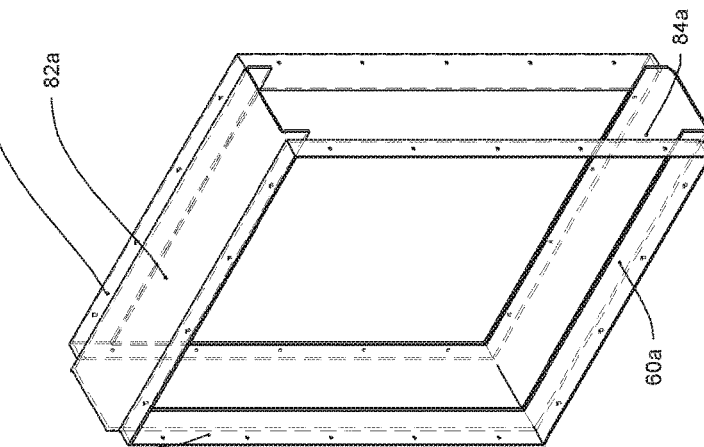
FIG. 21E is a perspective view of the filter frame shown in FIG. 18A
Figure 21D:
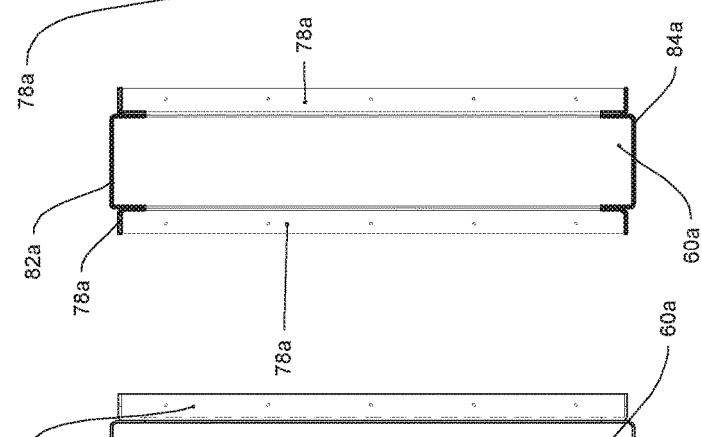
FIG. 21D is a section view of the filter frame shown in FIG. 18A, taken from A-A shown in FIG. 21B.
Figure 21C:
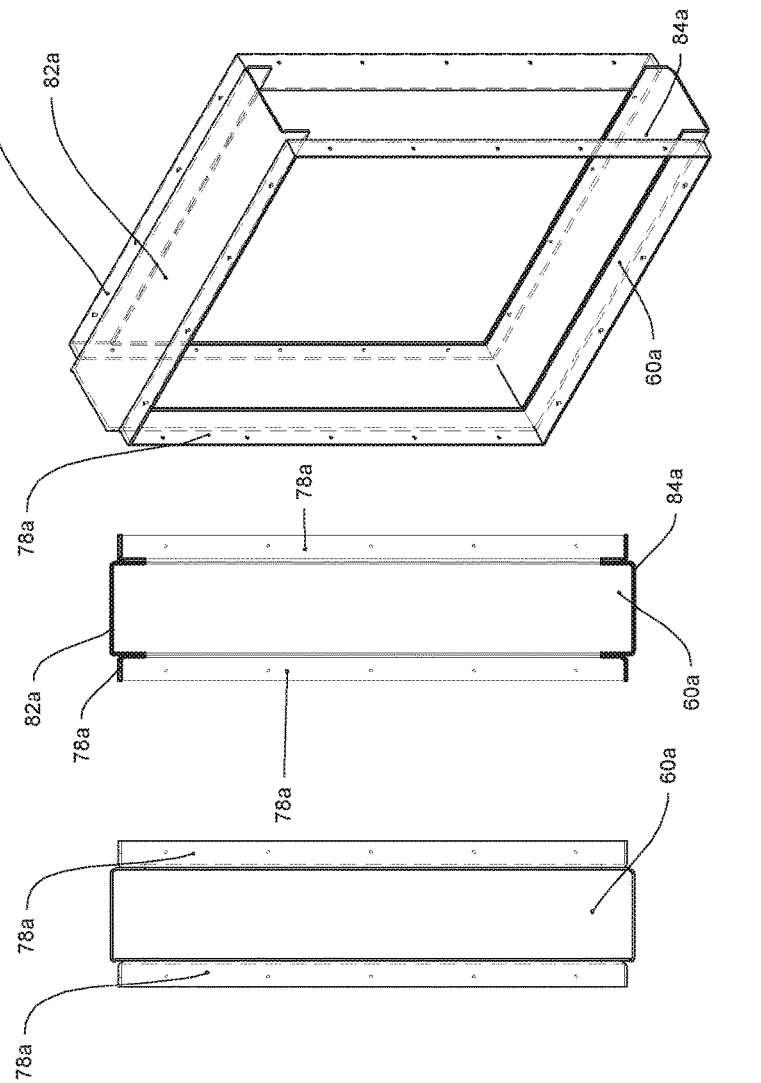
FIG. 21C is a side view of the filter frame shown in FIG. 18A
Figure 21A:
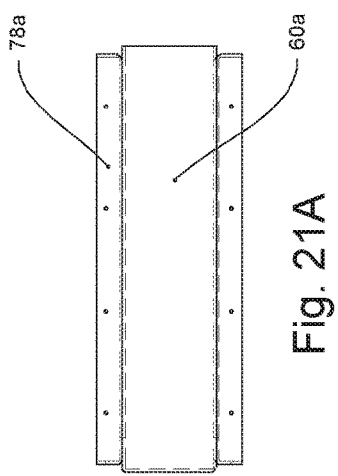
FIG. 21A is a top view of the filter frame shown in FIG. 18A
Figure 21B:
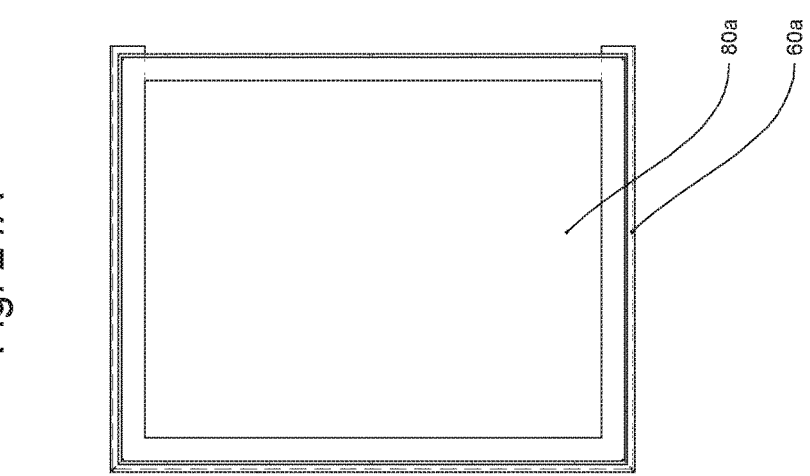
FIG. 21B is a front view of the filter frame shown in FIG. 18A
Figure 25C:
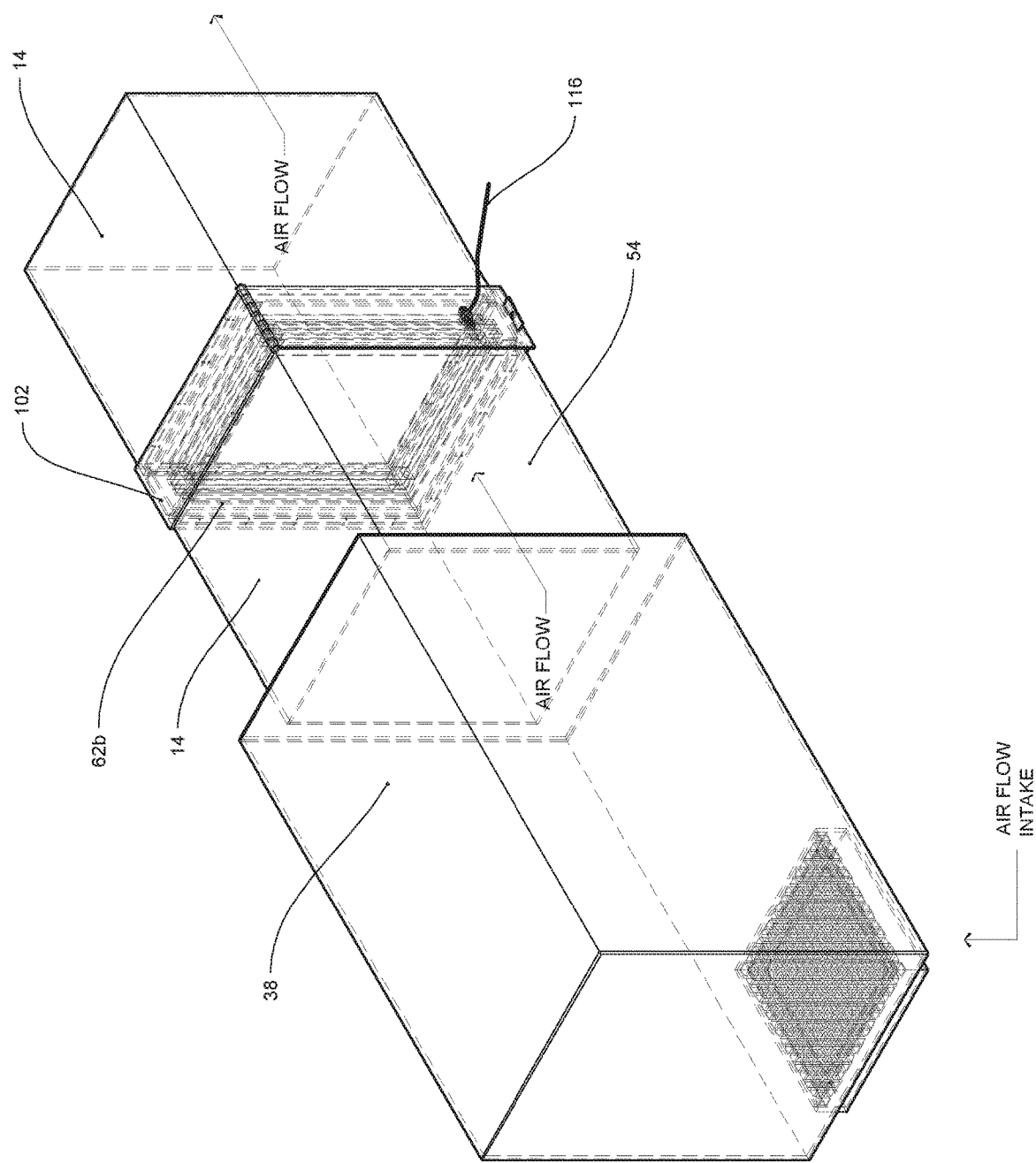
FIG. 25C is a perspective view of the interchangeable ultraviolet system.
Figure 27B:
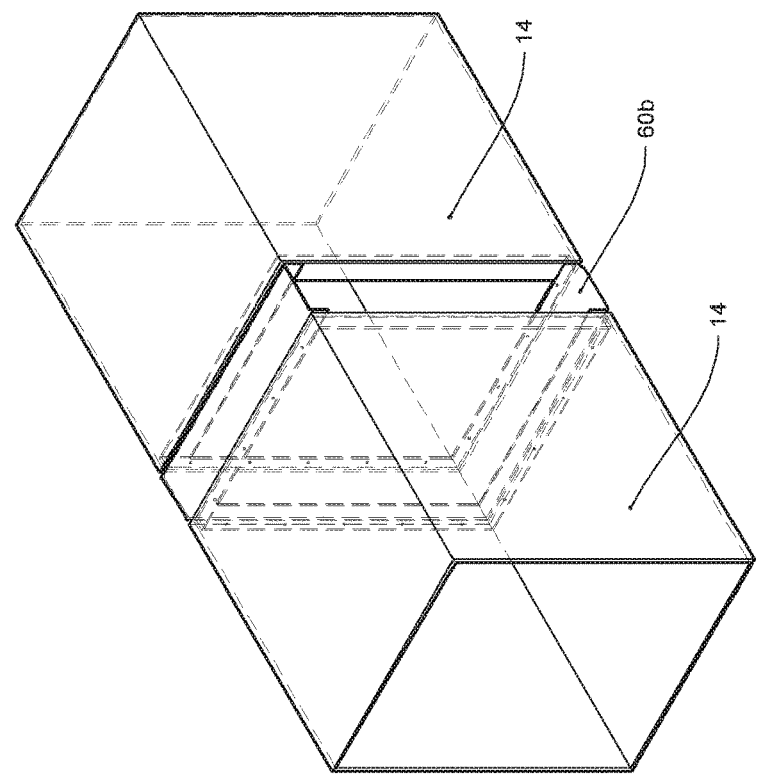
FIG. 27B is a perspective view of the mounted ultraviolet frame for the interchangeable ultraviolet system.
Figure 27A:
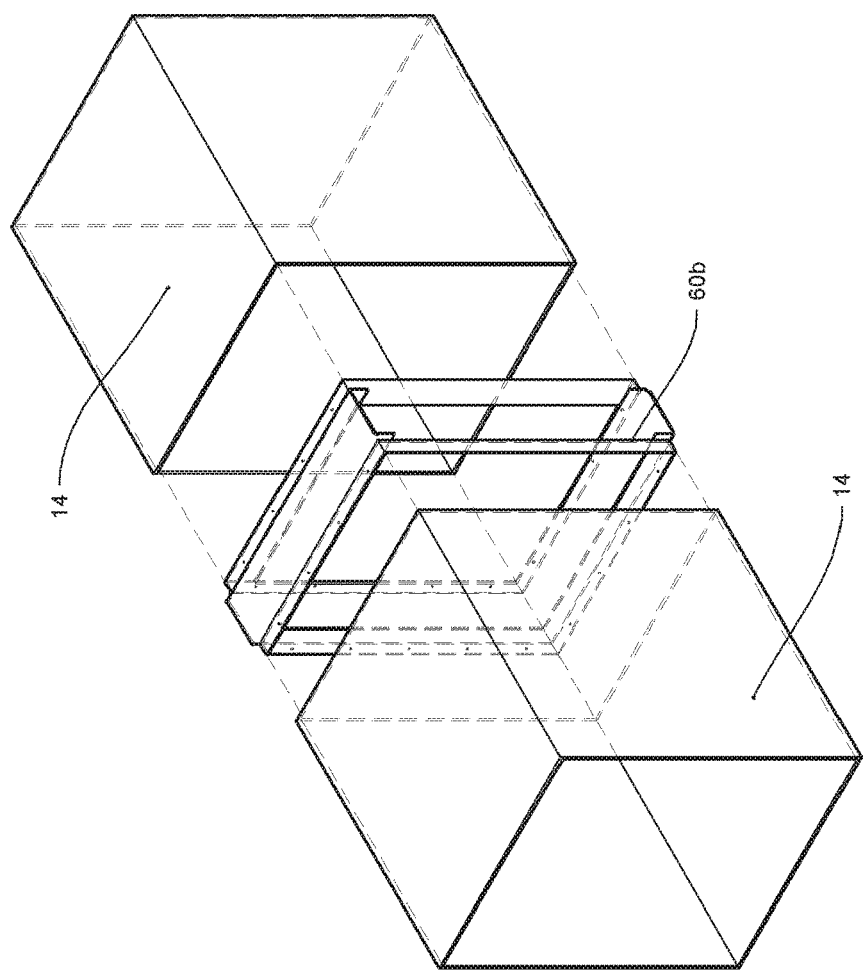
FIG. 27A is a perspective view of the mounting for the ultraviolet frame for the interchangeable ultraviolet system.
Figure 27C:
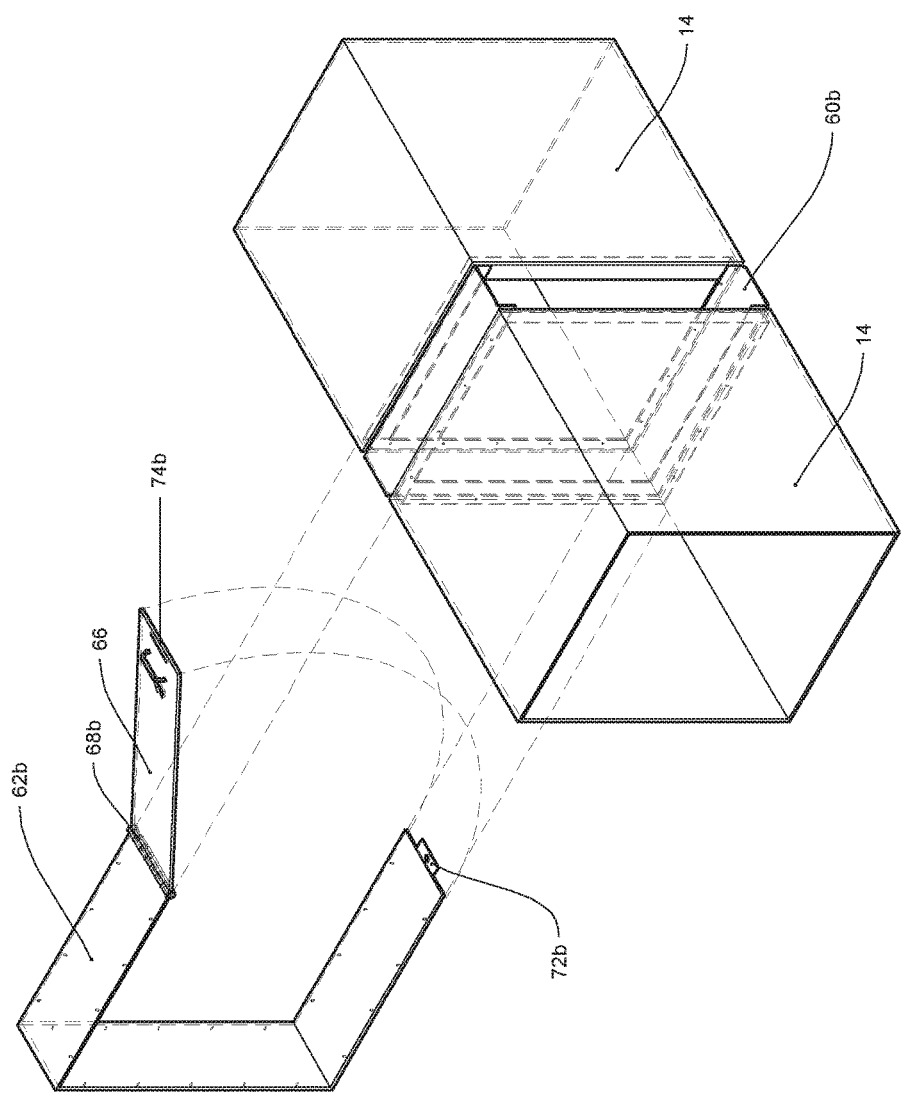
FIG. 27C is a perspective view of the disengaged mount clamp and door for the interchangeable ultraviolet system.
Figure 31A:
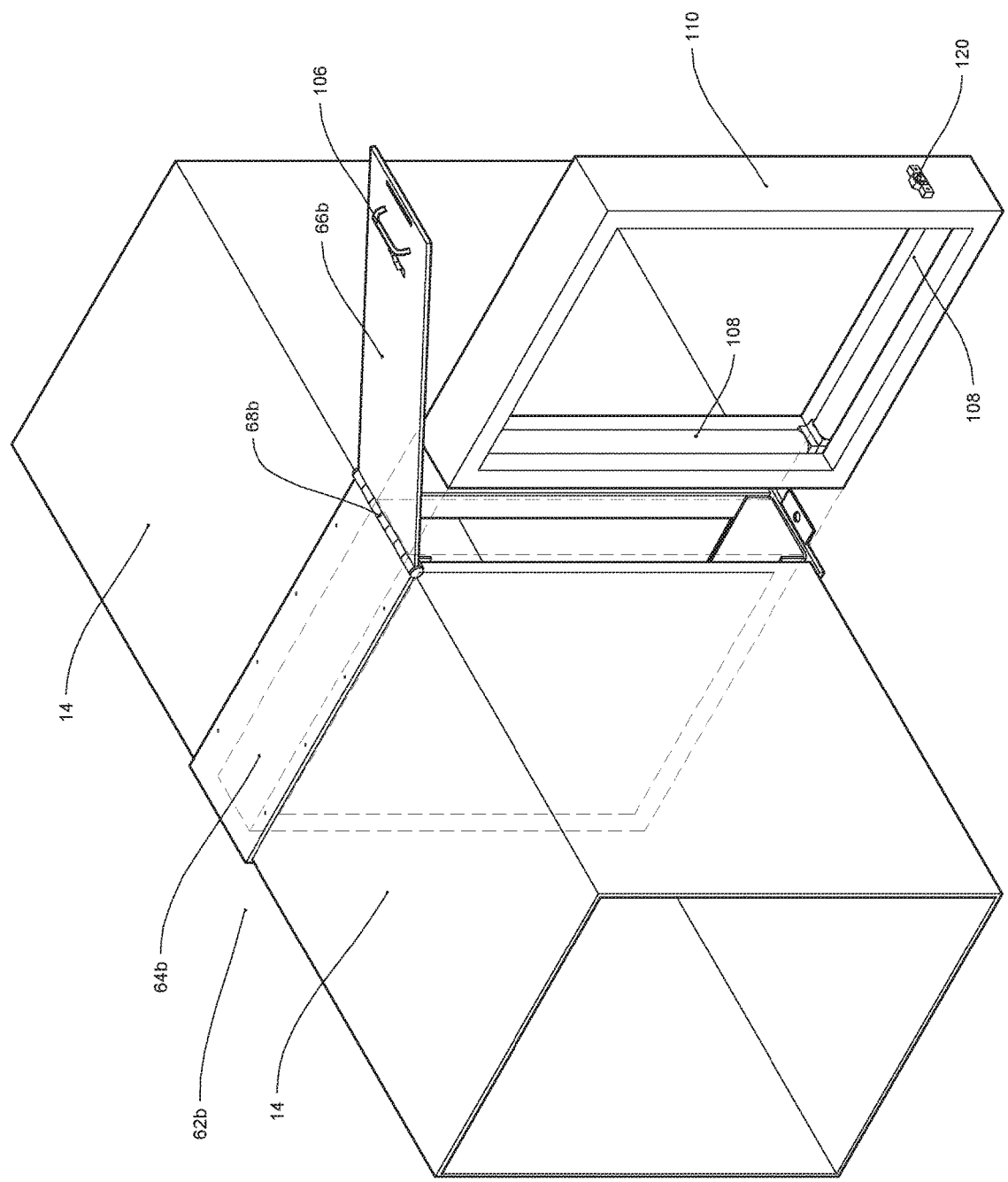
FIG. 31A is a perspective view of the ultraviolet system similar to FIGS. 27D and 27E.
Figure 31C:
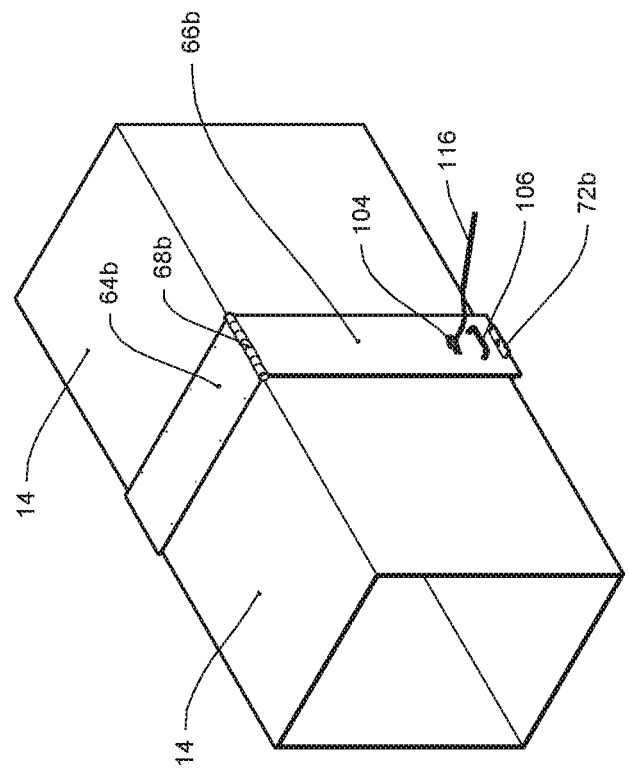
FIG. 31C is a perspective view of the ultraviolet system as shown in FIG. 31B with the attached power cord.
Figure 31B:
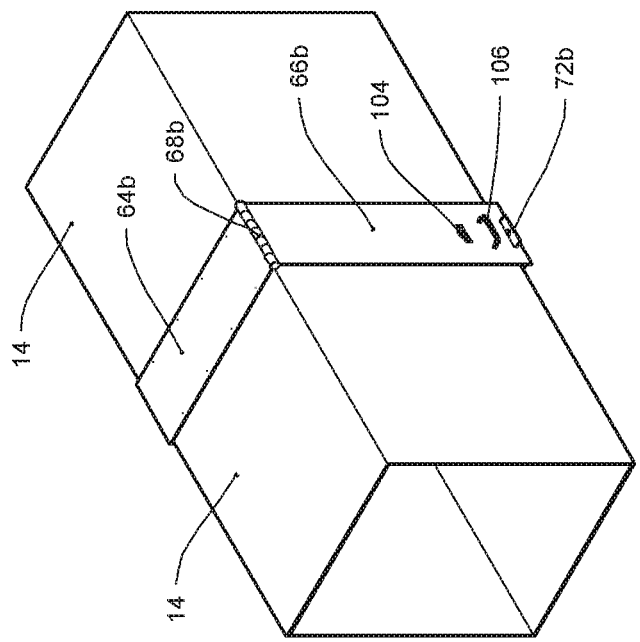
FIG. 31B is a perspective view of the ultraviolet system of FIG. 31A with the door securely closed.

In a third system, shown primarily in FIGS. 16A-16C, and also shown in FIGS. 17-26, a filter 32 with three-dimensional webbing 92, the actual filter 32 will look more like graphing paper, just extended in the z axis to provide depth and more importantly, increased surface area to collect pathogens circulating throughout the ducts. This may be seen primarily in FIGS. 19A-19C and 22A-24C. The filter 32 will be dipped into an antimicrobial solution and then dried. Once installed the filter 32 will catch traveling pathogens. The filter 32 will require replacement periodically. The filter 32 can be installed in multiple locations to enhance its functionality. For example, placing one filter 32 inside the condenser and one at the supply vent 13a, the air can be filtered twice before entering a room.

In an embodiment of the system 10, the invention provides for a system for disinfecting air circulated in an HVAC system. The system includes a multi-phase system, wherein the multi-phase system comprises at least six segments, with at least one segment representing each of at lease one air intake 12, at least one air handler 38, and at least one connecting ductwork 14.

The system also includes an arrangement of the at least six segments that correlates to six phases. Phase 1 is the air return 40 of an HVAC system; phase 2 is the plurality of ultraviolet lights 114 including an ultraviolet light array 108 before the air handler 38. The ultraviolet light array 108 comprises at least one ultraviolet light 114 in the plurality of ultraviolet lights 108. Phase 3 is the air handler 38. Phase 4 is a second ultraviolet array 108 comprising at least one ultraviolet light 114 in the plurality of ultraviolet lights 108 in the supply ductwork 14 after the air handler 38. Phase 5 is the airborne disinfecting system 36/32, and phase 6 is an air supply 13 of an HVAC system. The at least one connecting ductwork 14 is further defined as ductwork 14 connecting each of the six phases.

The system has at least one interchangeable filter 32, wherein each filter 32 in the at least one interchangeable filter 32 is an elongate three-dimensional grid 92 with a series of openings 94/98 to allow circulated are to flow over the air filter's elongate surfaces 96. The interchangeable filter is pre-dipped in a disinfecting solution, which is allowed to dry on the surfaces 96 of the interchangeable filter 32 to thereby kill any pathogen that may come in contact with the surfaces 96. The interchangeable filter 32 is located in a filter housing 62a, wherein the filter housing 62a connects two segments of the ductwork 14 and the filter housing 62a is contoured to align with perimeter dimensions of the ductwork 14. Perimeter dimensions mean that the filter housing has the same width and height as the ductwork 14 so that the edges meet flush.

Further, the filter housing 62a defining a four-walled metallic segment 62a, as shown in FIGS. 20A-20D with openings correlating to each of the two segments of ductwork 14. A closeable opening is created for insertion of the filter 32 therein created by a hinge 68a moveably coupling one wall 64a of the four-walled metallic segment 62a thereby creating a hinged flap 66a. Once the flap 66a is closed, the flap 66a seals an inside airflow channel 67 between each duct segment 14 connected by the four-walled metallic segment 62a.

Also shown in FIGS. 18A-21E are the door locking engagement mechanism 70a made of a flange with aperture 72a and an opening for the flange with the aperture 74a. Filter frame screws 76a are shown to provide securement of the filter frame 60a. Filter frame mounting flange 78a allows the filter frame 60a to mount within the ductwork 14 and filter frame housing 62a. Each frame 60a contains an opening 80a that correlates to the opening on the filter frame housing, and thereby allows passage of airflow through the ducts 14 and filter frame 60a. In addition, for structural support in guiding a filter 32 in each filter frame 60a, the filter frame 60a includes an inverted U-shaped channel 82a on top portion of the frame 60a and a U-shaped channel 84a on a bottom portion of said filter frame 60a. These channels 82a/84a guide the filter 32 during insertion.

In addition, FIGS. 22A-24C show a first embodiment filter 86, a second embodiment filter 88, and a third embodiment filter 90, each having individual cells 92 with an opening 98 and an exit 100.

The surfaces 96 of these interchangeable filters 32 are periodically sprayed with a disinfecting solution expelled through the nozzles 20 of the disinfecting system 36. This disinfectant solution thereby kills any pathogen that may come in contact with the surfaces 96 of the interchangeable filter 32.

Similarly, the housing 62b of the ultraviolet segment 108 resembles the housing 62a of the filter 32 segment. This is so filters 32 and ultraviolet arrays 108 may be swapped out as needed. Keep in mind, however, that ultraviolet arrays 108 should not be swapped in to an area that is in direct relation to spray nozzles 20. As may be appreciated in FIGS. 25A-31C, the ultraviolet filter segment also contains a frame 60b, frame housing 62b, housing structural frame 64b, flap 66b, hinge 68b, flap locking engagement mechanism 70b, flange with aperture 72b, opening for flange in flap 74b, frame screws 76b, mounting flange 78b, opening 80b, upper channel 82b, and lower channel 84b. Also shown is a power aperture 104 in the flap 66b, a flap handle 106, electrical feed 116, electrical feed screws 118, and an electrical inlet 120.

In some embodiments, the at least one spray nozzle 20 is mounted inside the connecting duct 14. In other embodiments, the at least one spray nozzle 20 is mounted outside the connecting duct 14 and extends through an aperture 16 of the connecting duct 14.

The airborne disinfecting system further includes a spray ring 18 defined by a perimeter hose 18 connecting the supply hose 22/48 to the at least one spray nozzle 20, wherein a plurality of spray nozzles 22 are mounted along the spray ring 18. The spray ring 18 may form a continuous loop surrounding the outer surface of the ductwork 14, and the spray nozzles 20 connected to the spray ring 18 extend through the apertures 16 in the duct work 14. These apertures 16 are then sealed by rubber gaskets 20a.

The system also has a plurality of ultraviolet lights 114, and an airborne disinfecting system with at least one spray nozzle 20 mounted to the at least one connecting duct 14, wherein a supply hose 22/48 connects the at least one spray nozzle 20 to at least one reservoir 24/44/46 of disinfectant. The plurality of ultraviolet lights 114 include segments of ultraviolet lights configured as a plurality in a ring formation 108 within an inner perimeter of the at least one connecting duct 14 and mounted along a width and a height of the inner perimeter of the at least one connecting duct 14.

While there has been shown and described above the preferred embodiment of the instant invention it is to be appreciated that the invention may be embodied otherwise than is herein specifically shown and described and that certain changes may be made in the form and arrangement of the parts without departing from the underlying ideas or principles of this invention as set forth in the Claims appended herewith.

We claim:

1. A system for disinfecting air circulated in an HVAC system, comprising:

a multi-phase system, wherein said multi-phase system comprises at least six segments, with at least one segment representing each of at least one air intake, at least one air handler, and at least one connecting ductwork;

at least one interchangeable filter, wherein each filter in said at least one interchangeable filter is an elongate three-dimensional grid with a series of openings to allow circulated air to flow over the air filter's elongate surfaces;

a plurality of ultraviolet lights;

an airborne disinfecting system with at least one spray nozzle mounted to said at least one connecting ductwork, wherein a supply hose connects said at least one spray nozzle to at least one reservoir of disinfectant;

said interchangeable filter is pre-dipped in a disinfecting solution which is allowed to dry on said surfaces of said interchangeable filter to thereby kill any pathogen that may come in contact with said surfaces;

said interchangeable filter is located in a filter housing, wherein said filter housing connects two segments of said ductwork and said filter housing is contoured to align with perimeter dimensions of said ductwork;

said filter housing defining a four-walled metallic segment with openings correlating to each of said two segments of ductwork; and a closeable opening for insertion of said filter therein created by a hinge moveably coupling one wall of said four-walled metallic segment thereby creating a hinged flap, whereby once closed, said flap seals an inside airflow channel between each ductwork segment connected by said four-walled metallic segment.

2. The system as recited in claim 1, further comprising:

an arrangement of said at least six segments correlating to six phases, wherein a phase 1 is an air return of the HVAC system, a phase 2 is said plurality of ultraviolet lights including an ultraviolet light array before the air handler, wherein said ultraviolet light array comprises at least one ultraviolet light in said plurality of ultraviolet lights, a phase 3 is said air handler, a phase 4 is a second ultraviolet array comprising at least one ultraviolet light in said plurality of ultraviolet lights in a supply ductwork after the air handler, a phase 5 is the airborne disinfecting system, and phase 6 is an air supply of an HVAC system; and said at least one connecting ductwork connects each phase in said six phases.

3. The system as recited in claim 1, wherein said surfaces of said interchangeable filter are periodically sprayed with the disinfectant expelled through said at least one spray nozzle to thereby kill any pathogen that may come in contact with said surfaces of said interchangeable filter.

4. The system as recited in claim 1, wherein said plurality of ultraviolet lights include segments of ultraviolet lights configured in a ring formation within an inner perimeter of said at least one connecting ductwork and mounted along a width and a height of said inner perimeter of said at least one connecting ductwork.

5. The system as recited in claim 1, wherein said at least one spray nozzle is mounted inside said connecting ductwork.

6. The system as recited in claim 1, wherein said at least one spray nozzle is mounted outside said connecting ductwork and extends through an aperture of said connecting ductwork.

7. The system as recited in claim 6, wherein said airborne disinfecting system with at least one spray nozzle mounted through said at least one connecting ductwork, further includes a spray ring defined by a perimeter hose connecting said supply hose to said at least one spray nozzle, wherein a plurality of spray nozzles are mounted along said spray ring.

8. The system as recited in claim 7, wherein said spray ring forms a continuous loop surrounding the outer surface of said ductwork, and said spray nozzles connected to said spray ring extend through apertures in the ductwork and are sealed by rubber gaskets.

9. A system for disinfecting air circulated in an HVAC system, comprising:
   a multi-phase system, wherein said multi-phase system comprises at least six segments, with at least one segment representing each of at least one air intake, at least one air handler, and at least one connecting ductwork;
   at least one interchangeable filter, wherein each filter in said at least one interchangeable filter is an elongate three-dimensional grid with a series of openings to allow circulated air to flow over the air filter's elongate surfaces;
   a plurality of ultraviolet lights;
   an airborne disinfecting system with at least one spray nozzle mounted to said at least one connecting ductwork, wherein a supply hose connects said at least one spray nozzle to at least one reservoir of disinfectant;
   said at least one spray nozzle is mounted outside said connecting ductwork and extends through an aperture of said connecting ductwork;
   said airborne disinfecting system with at least one spray nozzle mounted through said at least one connecting ductwork further includes a spray ring defined by a perimeter hose connecting said supply hose to said at least one spray nozzle, wherein a plurality of spray nozzles are mounted along said spray ring; and
   wherein said spray ring forms a continuous loop surrounding the outer surface of said ductwork, and said spray nozzles connected to said spray ring extend through apertures in the ductwork and are sealed by rubber gaskets.

* * * * *